(12) United States Patent
Ewers et al.

(10) Patent No.: US 11,253,672 B2
(45) Date of Patent: Feb. 22, 2022

(54) SLEEP APNEA TREATMENT SYSTEM AND IMPROVEMENTS THERETO

(71) Applicant: Fresca Medical Inc., San Clemente, CA (US)

(72) Inventors: Richard Ewers, Fulterton, CA (US); Andrew Dominguez, San Clemente, CA (US)

(73) Assignee: FRESCA MEDICAL, INC., San Clemente, CA (US)

( * ) Notice: Subject to any disclaimer, the term of this patent is extended or adjusted under 35 U.S.C. 154(b) by 0 days.

(21) Appl. No.: 16/034,967

(22) Filed: Jul. 13, 2018

(65) Prior Publication Data

US 2018/0326173 A1    Nov. 15, 2018

Related U.S. Application Data

(63) Continuation-in-part of application No. 15/557,907, filed on Sep. 13, 2017, and a continuation-in-part of
(Continued)

(51) Int. Cl.
*A61M 16/20* (2006.01)
*A61M 16/00* (2006.01)
(Continued)

(52) U.S. Cl.
CPC ......... *A61M 16/205* (2014.02); *A61B 5/6803* (2013.01); *A61M 16/0003* (2014.02);
(Continued)

(58) Field of Classification Search
CPC ............ A61M 16/208; A61M 16/0816; A61M 16/0683; A61M 16/0666; A61M 16/024;
(Continued)

(56) References Cited

U.S. PATENT DOCUMENTS 3,242,921 A     3/1966  Seeler
2008/0078395 A1  4/2008  Ho et al.
(Continued)

FOREIGN PATENT DOCUMENTS

EP          1466643 A1 * 10/2004  ........ A61M 16/0075
EP          1466643 A1    10/2004
WO       2000/038772 A1    7/2000

OTHER PUBLICATIONS

International Search Report and Written Opinion issued in PCT/US2018/42044 dated Nov. 9, 2018 (13 pages).

*Primary Examiner* — Kendra D Carter
*Assistant Examiner* — Arielle Wolff
(74) *Attorney, Agent, or Firm* — Manuel de la Cerra

(57) ABSTRACT

A valve structure for treating a patient suffering from obstructive sleep apnea is provided. The valve structure is connected to an air flow generator and is connected to a mask that covers at least the nostrils of a patient. The valve structure includes an inlet pressure port attached to the air flow generator and an expiration valve that includes an expiratory membrane, a primary seat and a secondary seat. During inspiration, the expiratory membrane forms a seal with the primary seat, and during expiration, the expiratory membrane forms a seal with the secondary seat.

25 Claims, 28 Drawing Sheets

Expiration Mode With Pressurized Flow

Related U.S. Application Data application No. 15/910,937, filed on Mar. 2, 2018, now Pat. No. 10,980,958, and a continuation-in-part of application No. 15/334,243, filed on Oct. 25, 2016, now Pat. No. 10,206,571.

(60) Provisional application No. 62/532,240, filed on Jul. 13, 2017, provisional application No. 62/465,905, filed on Mar. 2, 2017, provisional application No. 62/311,804, filed on Mar. 22, 2016, provisional application No. 62/694,126, filed on Jul. 5, 2018.

(51) Int. Cl.
*A61M 16/06* (2006.01)
*A61M 16/08* (2006.01)
*A61B 5/00* (2006.01)

(52) U.S. Cl.
CPC ...... *A61M 16/024* (2017.08); *A61M 16/0666* (2013.01); *A61M 16/0683* (2013.01); *A61M 16/0816* (2013.01); *A61M 16/204* (2014.02); *A61M 16/208* (2013.01); *A61B 5/4809* (2013.01); *A61M 16/0066* (2013.01); *A61M 16/0875* (2013.01); *A61M 2016/0027* (2013.01); *A61M 2205/3569* (2013.01); *A61M 2205/3592* (2013.01); *A61M 2205/42* (2013.01); *A61M 2205/8206* (2013.01); *A61M 2230/06* (2013.01); *A61M 2230/18* (2013.01); *A61M 2230/30* (2013.01); *A61M 2230/42* (2013.01); *A61M 2230/50* (2013.01); *A61M 2230/63* (2013.01); *A61M 2230/65* (2013.01)

(58) Field of Classification Search
CPC ............ A61M 16/0003; A61M 16/204; A61M 16/0066; A61M 2230/65; A61M 2230/63; A61M 2230/50; A61M 2230/42; A61M 2230/30; A61M 2230/18; A61M 2230/06; A61M 2205/8206; A61M 2205/42; A61M 2205/3592; A61M 16/0875; A61M 2205/3569; A61M 2016/0027; A61M 6/0672; A61M 16/08; A61M 16/0858; A61M 16/20; A61M 16/206; A61M 16/207; A61M 16/209; A61M 16/205–209; A61B 5/6803; A61B 5/4809; Y10T 137/7838; Y10T 137/7891; Y10T 137/7842; Y10T 137/7888; Y10T 137/7841; Y10T 137/86574
See application file for complete search history.

(56) References Cited

U.S. PATENT DOCUMENTS

| | | | | |
|---|---|---|---|---|
| 2011/0259331 | A1* | 10/2011 | Witt | A61M 16/20 128/204.18 |
| 2012/0266873 | A1* | 10/2012 | Lalonde | A61M 16/0069 128/201.13 |
| 2012/0285460 | A1* | 11/2012 | Smith | A61M 16/20 128/205.24 |
| 2014/0144447 | A1* | 5/2014 | Kuypers | A61M 16/0875 128/205.24 |
| 2014/0246025 | A1* | 9/2014 | Cragg | A61M 16/06 128/204.19 |
| 2014/0305431 | A1* | 10/2014 | Holley | A61M 16/1045 128/201.13 |
| 2016/0030229 | A1 | 2/2016 | Goldschmidt et al. | |
| 2016/0051791 | A1* | 2/2016 | Ewers | A61M 16/0057 128/204.23 |

\* cited by examiner

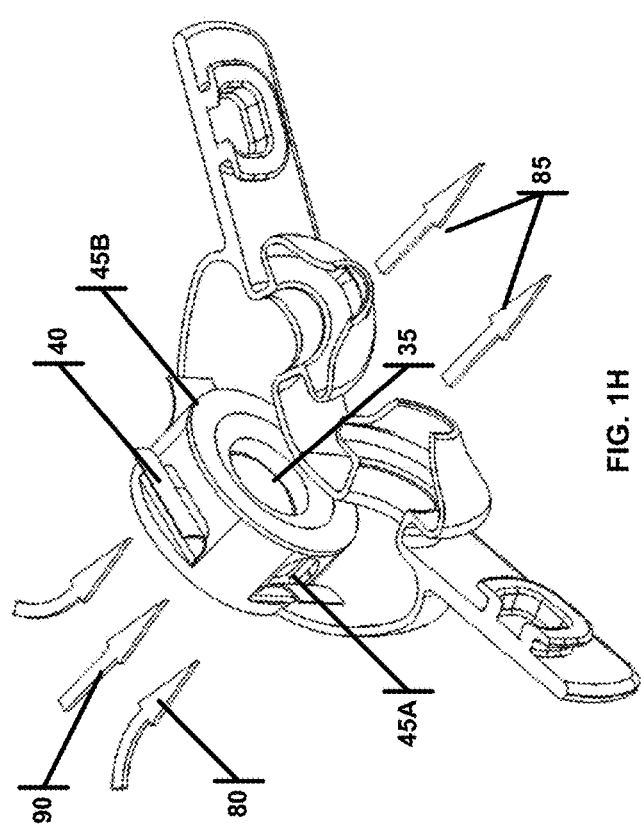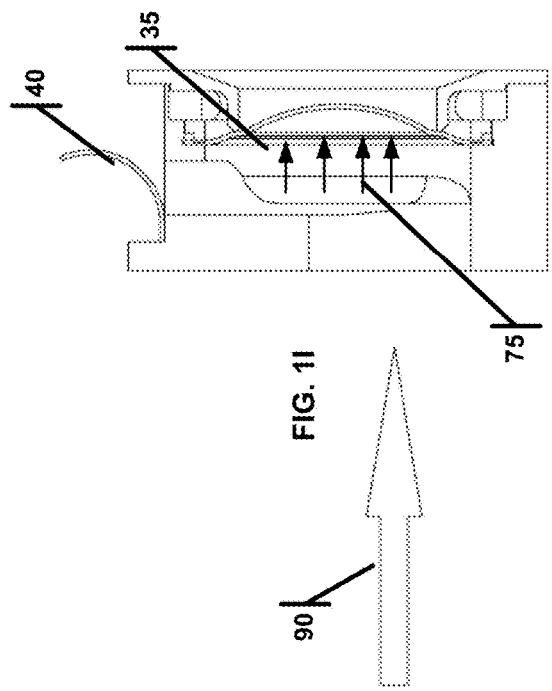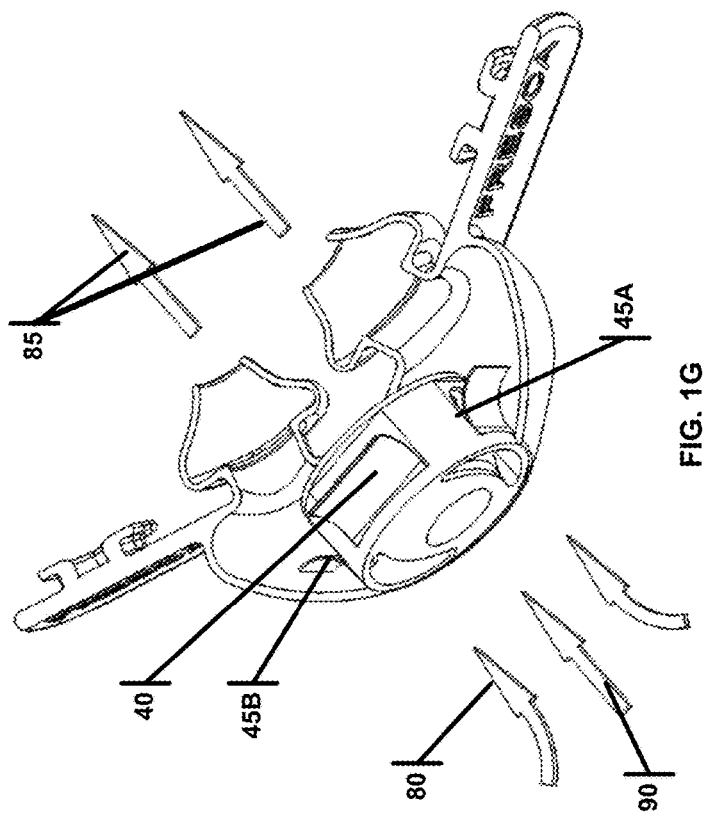

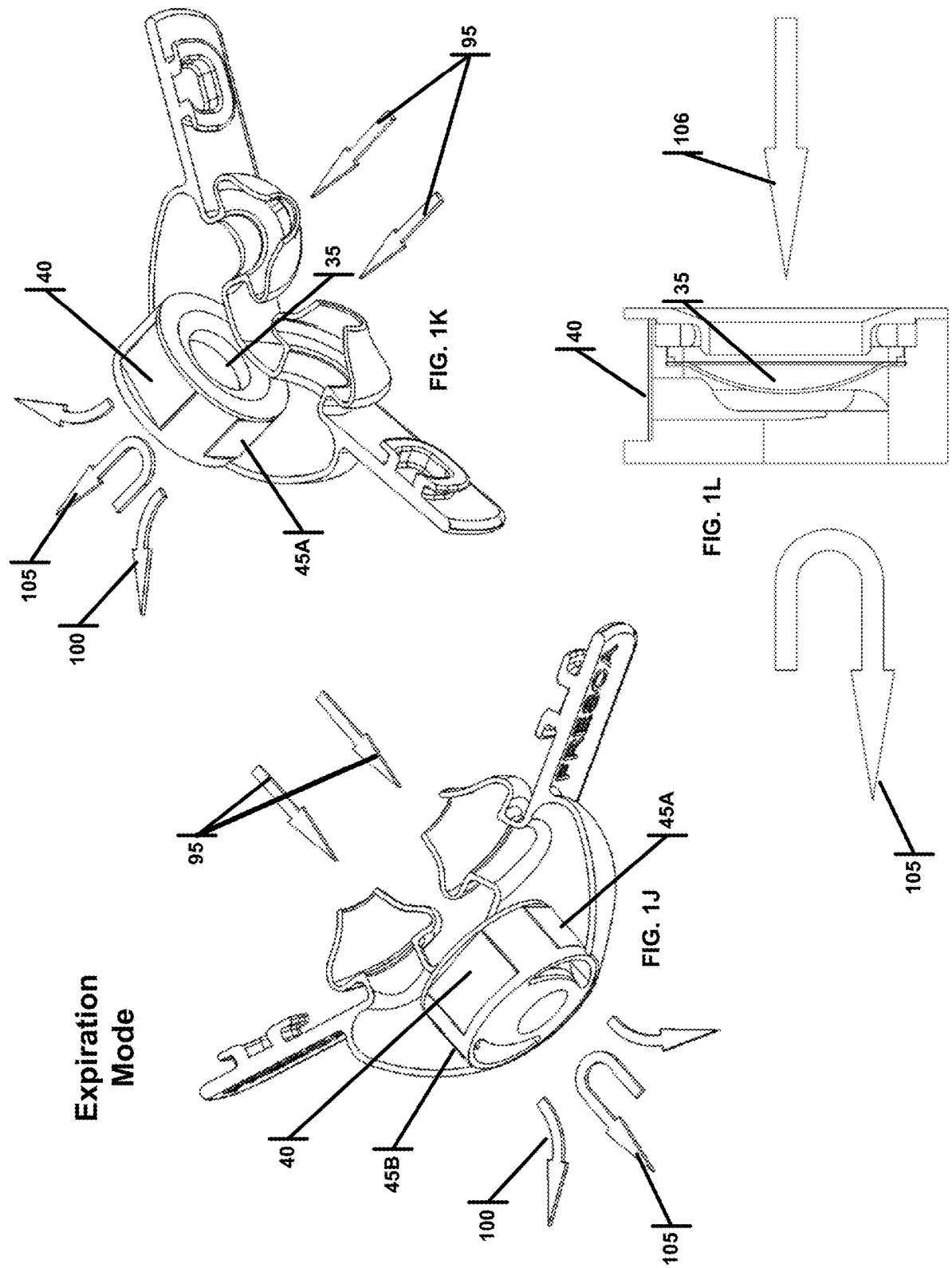

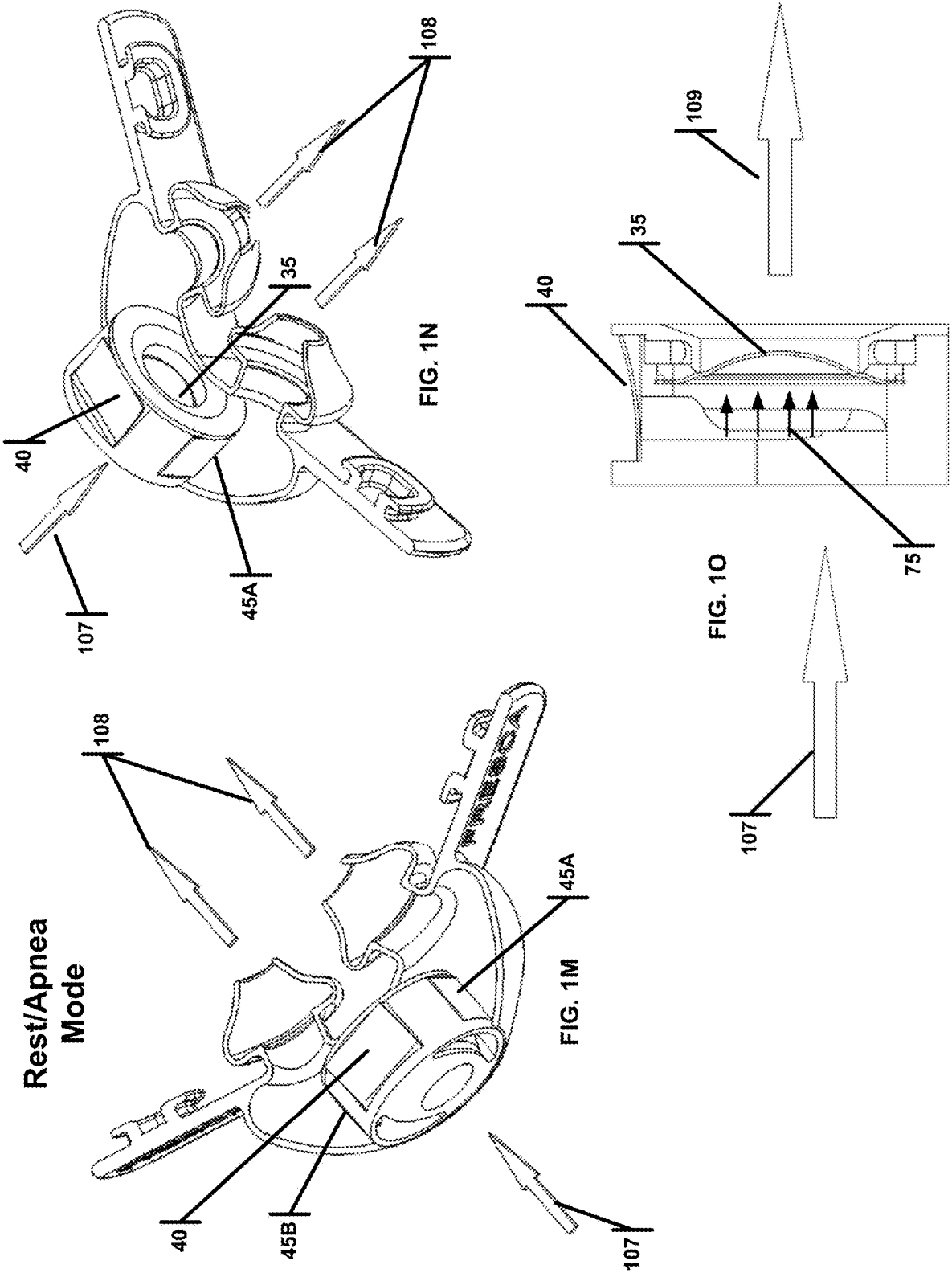

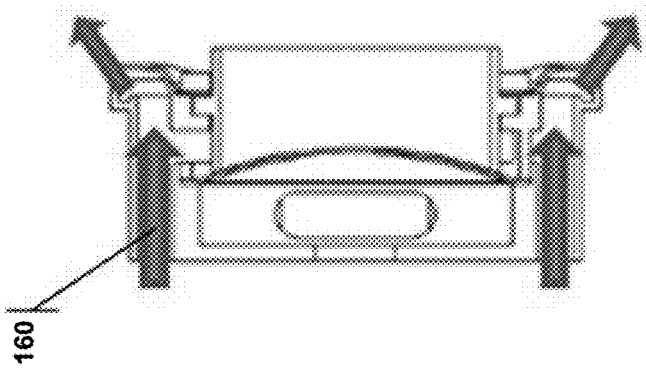
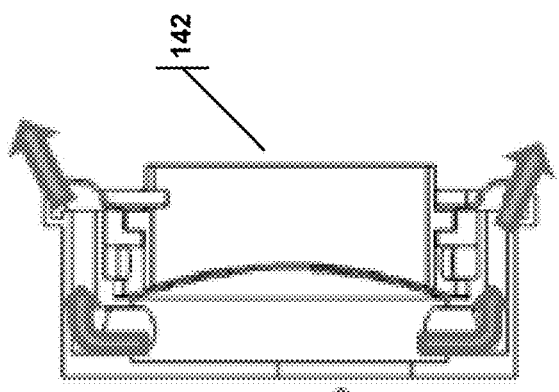
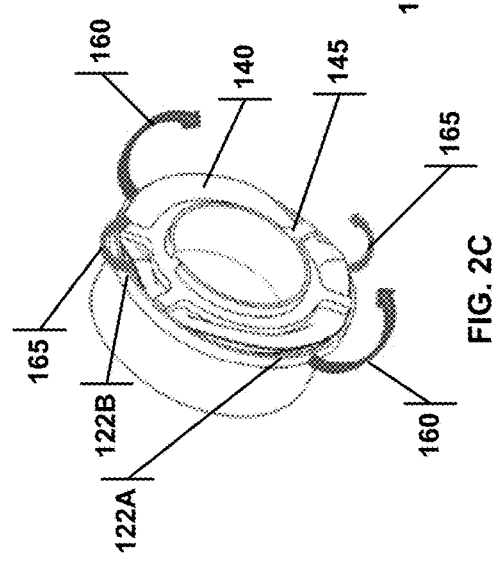
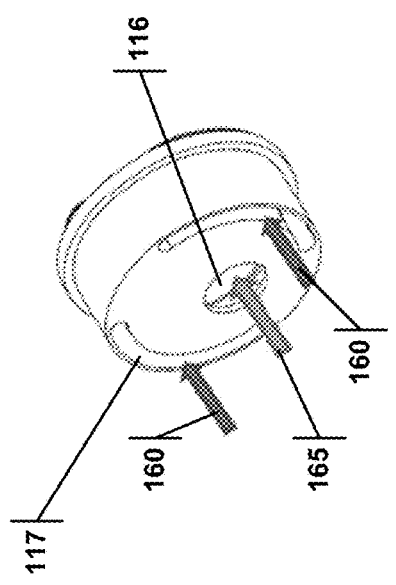
FIG. 2F Fresh Air
FIG. 2E Blower Air
FIG. 2C
FIG. 2D
INSPIRATION MODE Patient Exhalation Blower Air

EXPIRATION MODE

Blower Air

Blower Air

APNEA MODE

Inspiration Mode

Expiration Mode

Rest/Apnea Mode

Inspiration -
Disconnected
Mode

Expiration -
Disconnected
Mode

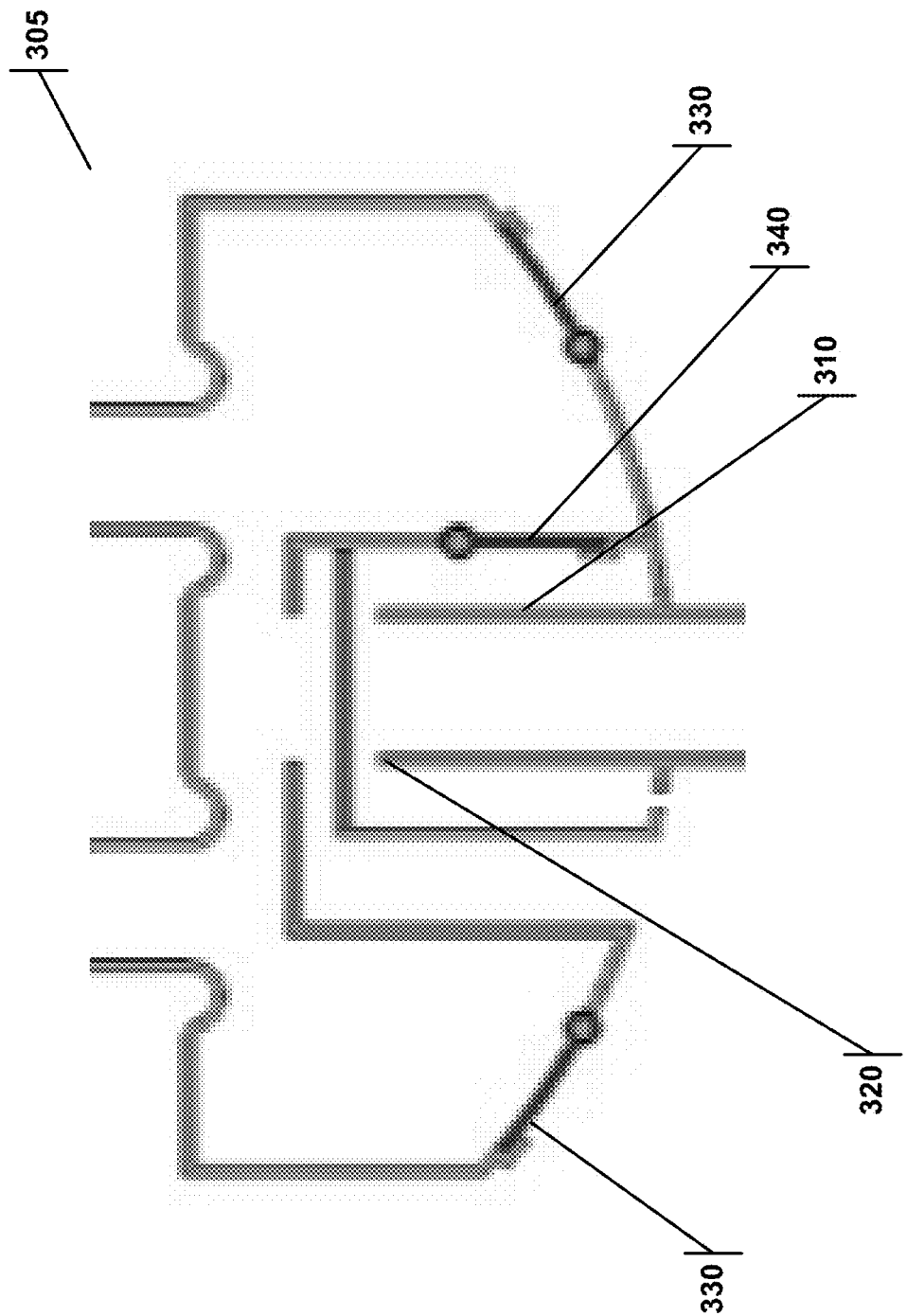

Inspiration Mode With Pressurized Flow

Expiration Mode With Pressurized Flow

Rest/Apnea Mode With Pressurized Flow

Inspiration – Disconnected
Mode

Expiration – Disconnected
Mode

SLEEP APNEA TREATMENT SYSTEM AND IMPROVEMENTS THERETO

RELATED APPLICATIONS

This application claims priority to U.S. Provisional Application No. 62/532,240 filed Jul. 13, 2017 titled "Sleep Apnea Treatment System and Improvements Thereto". This application also claims priority as a continuation-in-part to U.S. patent application Ser. No. 15/557,907, filed on Sep. 13, 2017 and titled "Apparatus, Systems, And Methods For Treating Obstructive Sleep Apnea", which in turn claims priority to PCT/US2016/023798, filed on Mar. 23, 2016 and titled "Apparatus, Systems, And Methods For Treating Obstructive Sleep Apnea", which in turn claims priority to U.S. patent application Ser. No. 14/930,284, filed on Nov. 2, 2015 and titled "Apparatus, Systems, And Methods For Treating Obstructive Sleep Apnea". This application also claims priority as a continuation-in-part to U.S. patent application Ser. No. 15/910,937, filed on Mar. 2, 2018 and titled "Sound Mitigation Structures and Methods for Use in Treating Obstructive Sleep Apnea", which in turn claims priority to U.S. Provisional Application No. 62/465,905, filed on Mar. 2, 2017 and titled "Sound Mitigation/Flow Optimization in a Valved Obstructive Sleep Apnea Treatment Mask". This application also claims priority as a continuation-in-part to U.S. patent application Ser. No. 15/334,243, filed on Oct. 25, 2016 and titled "Apparatus, Systems, And Methods For Treating Obstructive Sleep Apnea", which in turn claims priority to U.S. Provisional Application No. 62/311,804, filed on Mar. 22, 2016 and titled "Improvements to Sleep Apnea System." This application also claims priority to U.S. Provisional application No. 62/694,126, filed on Jul. 5, 2018 and titled "Braided Hose For Use In Sleep Apnea Treatment Systems That Decouples Forces." All of the foregoing applications are hereby incorporated by reference in their entirety.

The assignee of this application, FRESCA Medical, has described various embodiments of its valved Positive Airway Pressure (PAP) sleep apnea treatment mask. Those embodiments are described in U.S. patent application Ser. No. 13/860,926, filed Apr. 11, 2013, titled "Sleep Apnea Device," U.S. Provisional Application Ser. No. 61/623,855, filed Apr. 13, 2012, titled "Sleep Apnea Device," U.S. Provisional Application Ser. No. 61/775,430, filed Mar. 8, 2013, titled "Sleep Apnea Device," U.S. Provisional Application No. 61/823,553, filed May 15, 2013, titled "Sleep Apnea Device," U.S. Provisional Application No. 61/838,191, filed Jun. 21, 2013, titled "Sleep Apnea Device," U.S. Provisional Application No. 61/962,501, filed Nov. 8, 2013, titled "Sleep Apnea Device," U.S. Provisional Application No. 61/909,956, filed Nov. 27, 2013, titled "Sleep Apnea Device," U.S. Provisional Application No. 61/927,355, filed Jan. 14, 2014, titled "Valve with Pressure Feedback," U.S. Provisional Application No. 62/134,506 filed Mar. 17, 2015 titled "Valve with Pressure Feedback Draft Provisional Application," U.S. Provisional Application No. 62/163,601, filed May 19, 2015, titled "Airflow Generator with Delayed Onset", U.S. Provisional Application No. 62/184,787, filed Jun. 25, 2015 titled "Sleep Apnea Device," U.S. Provisional Application No. 62/239,146, filed Oct. 8, 2015 titled "Sleep Apnea Device," U.S. patent application Ser. No. 14/930,284, filed Nov. 2, 2015, titled "Apparatus, System and Methods for Treating Obstructive Sleep Apnea", U.S. Provisional Application No. 62/246,339 filed Oct. 26, 2015, titled "Venting of a Valved CPAP Mask to Create a Comfortable Breathing Sensation", U.S. Provisional Application No. 62/246,489 filed Oct. 26, 2015. titled "Managing Sleep Apnea with Pulse Oximeters and With Additional Assessment Tools", U.S. Provisional Application No. 62/246,328 filed Oct. 26, 2015, titled "Novel Low Flow Technology Designed to Meet CPAP Efficacy", U.S. Provisional Application No. 62/246,477 filed Oct. 26, 2015, titled "Composite Construction Air Delivery Hose for USE with CPAP Treatment", U.S. Provisional Application No. 62/275,899 filed Jan. 7, 2016 titled "Valved Mask To Reduce and Prevent Snoring", U.S. Provisional Application No. 62/311,804 filed Mar. 22, 2016, titled "Improvements to Sleep Apnea Machine", U.S. Provisional Application No. 62/382,980 filed Sep. 2, 2016, titled "Dual Rotatable Hose For Use With CPAP Treatment", U.S. application Ser. No. 15/334,243 filed Oct. 15, 2016, titled "Apparatus, Systems, And Methods For Treating Obstructive Sleep Apnea", U.S. Provisional Application No. 62/532,240 filed Jul. 13, 2017, titled "Sleep Apnea Treatment System and Improvements Thereto", U.S. Provisional Application No. 62/595,529 filed Dec. 6, 2017, titled "Sleep Apnea Treatment System and Improvements Thereto", and U.S. Provisional Application No. 62/465,905 filed Mar. 2, 2017, titled "Sound Mitigation/Flow Optimization in a Valved Obstructive Sleep Apnea Treatment Mask", all of which are hereby incorporated by reference in their entirety. Disclosed in this document are particular features and structures that may be used in conjunction with the previously disclosed embodiments.

TECHNICAL FIELD

The present invention is related to medical systems, devices, and methods. More specifically, the invention is related to systems, devices and methods for treating obstructive sleep apnea or snoring.

BACKGROUND

Obstructive sleep apnea (OSA) is a common medical disorder that can be quite serious. It has been reported that approximately one in twenty-two Americans (about 12,000,000 people) suffer from OSA, and many cases go undiagnosed. Chronic fatigue has long been recognized as the hallmark of OSA, but more recently, large clinical studies have shown a strong link between OSA, strokes and death.

Obstructive sleep apnea is a condition in which the flow of air pauses or decreases during breathing while one is asleep because the airway has become narrowed, blocked, or floppy. (See FIG. 1A of published patent application US20140246025 A1 to Cragg et al., published Sep. 4, 2014, which is incorporated herein by reference, illustrating an airway during normal breathing, and FIG. 1B therein illustrating the airway A during OSA.) A pause in breathing is called an apnea episode, while a decrease in airflow during breathing is called a hypopnea episode. Almost everyone has brief apnea or hypopnea episodes while they sleep. In OSA, however, apnea episodes occur more frequently and last longer than in the general population. OSA has become an increasingly costly medical condition in recent years, as the disorder is more prevalent in obese people, and obesity has become significantly more prevalent. Unfortunately, the currently available options for treating OSA are not ideal.

A person with OSA usually begins snoring heavily soon after falling asleep. Often, the snoring gets louder. The snoring is then interrupted by a long silent period, during which there is no breathing. This is followed by a loud snort and gasp, as the person attempts to breathe. This pattern repeats. Many people wake up unrefreshed in the morning and feel sleepy or drowsy throughout the day. This is called excessive daytime sleepiness (EDS). People with sleep apnea may act grumpy or irritable, be forgetful, fall asleep while working, reading, or watching TV, feel sleepy or even fall asleep while driving, or have hard-to-treat headaches. OSA sufferers may also experience depression that becomes worse, hyperactive behavior (especially in children), or leg swelling (if severe).

The most widely used therapy for OSA is Continuous Positive Airway Pressure (CPAP). As shown in FIG. 2 of US20140246025 A1 to Cragg et al., a CPAP system 10 typically consists of a mask 12a-12c fitting in or over the nose or nose and mouth, an air pressurizing console 14, and a tube 16 connecting the two (typically a six-foot long hose with a 20 mm diameter bore). CPAP works by pressurizing the upper airway throughout the breathing cycle, essentially inflating the airway to keep it open and thus creating what is sometimes referred to as a "pneumatic splint." This flow is set at a pressure that has been predetermined through medical testing to be appropriate to create a pneumatic splint in the user's airway. This prevents airway collapse and allows the user to breathe without obstruction. Because the masks 12a-12c typically leak air, CPAP systems have to provide an airflow rate of up to 200 liters per minute (approximate figure based on unpublished data). The high airflow rate is needed for multiple reasons. First, all the air needed for breathing must come through the hose. Second, conventional masks have an intended leak built in for the purpose of constant "$CO_2$ washout." Third, these systems achieve the required pressure by using a high airflow rate to generate a back-pressure at the mask end where the air is leaking out. Unfortunately, this high flow rate makes breathing feel quite uncomfortable for many users and requires a relatively large, noisy pressurizing console 14. Additionally, the high required flow rates of CPAP often cause discomfort during exhalation due to increased resistance, as well as nasal dryness, dry mouth, ear pain, rhinitis, abdominal bloating and headaches.

The overwhelming shortcoming of CPAP is poor user compliance. Over half of all users who try CPAP stop using it. Users dislike the side effects mentioned above, as well as having to wear an uncomfortable, claustrophobic mask, being tethered to a pressurizing console, the noise of the console, traveling with a bulky device, and a loss of personal space in bed.

Many CPAP devices and alternatives to CPAP have been developed, but all have significant shortcomings. Less invasive attempts at OSA treatment, such as behavior modification, sleep positioning and removable splints to be worn in the mouth, rarely work. A number of different surgical approaches for treating OSA have also been tried, some of which are still in use. For example, Uvulopalatopharyngoplasty (UPPP) and Laser Assisted Uvula Palatoplasty (LAUP) are currently used. Surgical approaches, however, are often quite invasive and not always effective at treating OSA.

One alternative approach to OSA treatment is to provide a pneumatic splint during the expiratory portion of the respiratory cycle by producing a partial blockage in the nose or mouth, thus slowing the release of air during expiration and increasing positive pressure in the airway. The simplest way to form an expiratory pneumatic splint, pursing the lips, has been shown to open the upper airway and improve breathing in emphysema users. This type of maneuver is generically labeled Expiratory Positive Airway Pressure (EPAP).

Ventus Medical, Inc. (http://www.proventtherapy.com/ventus_medical) has developed a removable nasal EPAP device to produce such a pneumatic splint during exhalation (the Provent® Sleep Apnea Therapy). (See, for example, published patent application US20060150978 A1 to Doshi et al., published Jul. 13, 2006, which is incorporated herein by reference.) This device restricts exhalation by forcing expired air through several small orifices attached to the nose. This is labeled a Fixed Orifice Resistor (FOR). Shortcomings of this therapy are that 1) the fixed hole exhalation valve does not have a capped maximum pressure, 2) the pressure increases immediately upon exhalation and therefore makes it difficult to exhale, and 3) with no assistance of additional pressure from an external source, if the user has an apneic event there is no 'rescue pressure'—i.e., the flow supplied by the blower box. A further disadvantage is that the Provent® device or any FOR restricts expiratory airflow using a fixed hole for resistance. This leads to an uncomfortable spike in nasal pressure at the beginning of expiration when airflow is highest and a less efficacious decrease in nasal pressure at the end of expiration when airflow is lowest. Another shortcoming of the Provent® device is that it produces the pneumatic splint only during exhalation—i.e., there is no increased pressure during inhalation.

In addition, the device is not effective in mouth breathers or users who become mouth breathers when resistance is added to the nasal passages. Thus, the Provent® device is useful only in moderate cases of OSA that do not convert to mouth breathing.

Although snoring is not as severe a condition as OSA, it does affect lives adversely. Snoring can adversely affect sleep quality and can make sleeping with a spouse or other partner difficult. Although many snoring therapies have been tried, including Breathe Right® Nasal Strips and more invasive approaches in more severe cases, no ideal solution has been found.

Therefore, it would be advantageous to have improved systems, devices and methods for treating OSA and snoring. Ideally, such systems, devices and methods would be less cumbersome than currently available CPAP systems, to improve user compliance. Also ideally, such systems, devices and methods would provide some of the advantages of an expiratory pneumatic splint. At least some of these objectives were met by the embodiments described in US20140246025 A1 to Cragg et al., previously incorporated herein by reference (herein sometimes referred to as "Cragg '025").

Cragg '025 utilized a novel system of valves to allow inspiration of air supplied via the hose and also from inlets in the mask that take in room air. In various example embodiments, Cragg '025 provided variable resistance to expiratory air flow using a resistive mechanism other than the infused external air that increases over the course of expiration, thus providing an easier, more comfortable start to expiration while maintaining airway pressure toward the end of expiration (e.g., by decreasing resistance to expiratory flow when intranasal pressure reaches a threshold pressure and/or by gradually increasing resistance to expiratory air flow until intranasal pressure reaches the threshold pressure). Another improvement in various embodiments of Cragg '025 was that lower air flow rates were used (e.g., less than or equal to 20 L/min), while still supplying the desired therapeutic pressure (e.g., between about 4 $cmH_2O$ and 20 $cmH_2O$), thus requiring less power and smaller device components than traditional CPAP and reducing side effects. Still another improvement of Cragg '025 was a less cumbersome, more form-fitting mask that reduced air leaks and was more comfortable to wear than prior CPAP masks and eliminated the need for high flow rates because there was no need to compensate for air leaks. Accordingly, the devices described therein could be used in connection with a small diameter hose (e.g., having a diameter of less than or equal to about 15 mm), thus decreasing the bulkiness of the system.

While Cragg '025 was an important improvement over the state of the art, it required and relied upon a special system of protruding valves that had to be pre-adjusted or set to suit each user. It would be advantageous to improve upon the system of Cragg '025 by making the system simpler and more compact in design, simpler to use, and more robust.

SUMMARY

Provided in various example embodiments is an improved apparatus, system, and method for treating obstructive sleep apnea. Specifically, a novel valve structure for treating a patient suffering from obstructive sleep apnea is provided. The valve structure is connected to an air flow generator and connected to a mask that covers at least the nostrils of a patient. The valve structure includes an inlet pressure port attached to the air flow generator and an expiration valve that includes an expiratory membrane, a primary seat and a secondary seat. During inspiration the expiratory membrane forms a seal with the primary seat, and during expiration the expiratory membrane forms a seal with the secondary seat.

The opening pressure of the expiratory valve may be variable and dependent on the pressure of air in the inlet pressure port as follows: (1) the opening pressure of the expiration valve increases when the pressure of air in the inlet pressure port increases; and/or (2) the opening pressure of the expiration valve decreases when the pressure of air in the inlet pressure port decreases.

The expiratory valve may have a standoff.

The valve structure may also include an inspiration valve constructed to allow air flow from the outside of the mask into the mask with little resistance and to block air flow from within the mask to the outside of the mask. The inspiration valve and the expiration valve may be fluidly connected to an ambient port.

The valve structure may also have an inlet pressure valve that is constructed to allow air flow from the air flow generator into the mask with little resistance and to block air flow from traveling from the mask to the air flow generator.

All of these valves may be part of a cartridge that is removable from the mask.

The valve structure may have an inspiration mode, a rest/apnea mode and an expiration mode. The inspiration mode occurs when the patient inspires air, during which the inspiration valve and the inlet pressure valve are open, and the expiratory membrane forms a seal with the primary seat. The rest/apnea mode occurs when the patient is neither inspiring air nor expiring air, during which the inlet pressure one-way-valve is open, the expiratory membrane forms a seal with the primary seat, and the inspiration valve is closed. The expiration mode occurs when the patient expires air, during which the expiratory membrane forms a seal with the secondary seat, and the inlet pressure valve and the inspiration valve are closed.

The valve structure may have a disconnected mode when the air flow generator is not providing airflow to the valve structure, during which, when a patient inspires, the inspiration valve opens and the expiratory membrane forms a seal with the primary seat. Additionally, when a patient expires, the inspiration valve is closed, and the expiratory membrane forms a seal with the secondary seat.

The valve structure may be part of a larger system. The system may include a controller that delays the operation of the blower box, and/or gradually increases the amount of pressure delivered by the blower box.

A valve structure for treating a patient suffering from obstructive sleep apnea is provided. The valve structure is connected to an air flow generator and is connected to a mask that covers at least the nostrils of a patient. The valve structure includes a housing with an inlet pressure port connected to the air flow generator, and an ambient pressure port. Within the housing is an expiratory membrane, an expiratory valve seat, an inspiratory membrane, an inlet pressure valve seat, an inspiratory valve seat, and an inspiratory membrane segmentation structure configured to segment the movement of the inspiratory membrane into at least a first portion and a second portion. An expiratory valve in fluid connection with the inlet pressure port is formed by the expiratory membrane and the expiratory valve seat. An inlet pressure valve is formed by the inlet pressure valve seat and the first portion of the inspiratory membrane, and the inlet pressure valve allows air flow from the inlet pressure port into the mask with little resistance and blocks air flow from within the mask to the inlet pressure port. An inspiratory valve is formed by the inspiratory valve seat and the second portion of the inspiratory membrane, and the inspiratory valve allows air flow from the ambient pressure port into the mask with little resistance and blocks air flow from within the mask to the ambient pressure port.

The expiratory valve seat and the inlet pressure valve seat may be integrally formed into the housing. The inspiratory membrane segmentation structure may further segment the movement of the inspiratory membrane into at least a third portion and a fourth portion. A second inlet pressure valve is formed by a second inlet pressure valve seat and the third portion of the inspiratory membrane. A second inspiratory valve is formed by a second inspiratory valve seat and the fourth portion of the inspiratory membrane. The second inlet pressure valve seat and the second inspiratory valve seat may be integrally formed into the housing.

The housing defines a housing center axis. The expiratory membrane is substantially planar and may be oriented substantially orthogonal to the housing center axis. Likewise, the inspiratory membrane is substantially planar and may be oriented substantially orthogonal to the housing center axis. The expiratory membrane may define an expiratory membrane center axis that is substantially coincident with the housing center axis. Likewise, the inspiratory membrane may define an inspiratory membrane center axis that is substantially coincident with the housing center axis.

The valve structure may have at least an inspiration mode, a rest/apnea mode and an expiration mode: the inspiration mode occurs when the patient inspires air, during which the inspiration valve and the inlet pressure valve are open, and the expiratory membrane forms a seal with the expiratory valve seat; the rest/apnea mode occurs when the patient is neither inspiring air nor expiring air, during which the inlet pressure valve is open, the expiratory membrane forms a seal with the expiratory valve seat, and the inspiration valve is closed; and the expiration mode occurs when the patient expires air, during which the expiratory valve is open and the inlet pressure valve and the inspiration valve are closed.

The valve structure may also have a disconnected mode when the air flow generator is not providing airflow to the valve structure during which, when a patient inspires, the inspiration valve opens, and when a patient expires, the inspiration valve is closed.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure. It will be understood that certain components and details may not appear in the figures to assist in more clearly describing the invention.

FIG. 1G is a front perspective sectional view of the example PAP apparatus of FIG. 1A, depicting operation during the inspiration mode according to various example embodiments.

FIG. 1H is a rear perspective sectional view of the example PAP apparatus of FIG. 1A, depicting operation during the inspiration mode according to various example embodiments.

FIG. 1I is a sectional side view taken through the middle of the example valve cartridge of FIG. 1B, depicting operation during the inspiration mode according to various example embodiments.

FIG. 1J is a front perspective sectional view of the example PAP apparatus of FIG. 1A, depicting operation during the expiration mode according to various example embodiments.

FIG. 1K is a rear perspective sectional view of the example PAP apparatus of FIG. 1A, depicting operation during the expiration mode according to various example embodiments.

FIG. 1L is a sectional side view taken through the middle of the example valve cartridge of FIG. 1B, depicting operation during the expiration mode according to various example embodiments.

FIG. 1M is a front perspective sectional view of the example PAP apparatus of FIG. 1A, depicting operation during the rest/apnea mode according to various example embodiments.

FIG. 1N is a rear perspective sectional view of the example PAP apparatus of FIG. 1A, depicting operation during the rest/apnea mode according to various example embodiments.

FIG. 1O is a sectional side view taken through the middle of the example valve cartridge of FIG. 1B, depicting operation during the rest/apnea mode according to various example embodiments.

FIG. 2BB illustrates in an exploded view of the various parts of a third embodiment of a novel valve structure for use in the treatment of sleep apnea.

FIG. 2C shows the fresh air flow and the blower air flow of the novel valve structure of FIG. 2A during inspiration.

FIG. 2D shows the fresh air flow and the blower air flow of the novel valve structure of FIG. 2A during inspiration.

FIG. 2E shows the blower air flow of the novel valve structure of FIG. 2A during inspiration.

FIG. 2F shows the fresh air flow of the novel valve structure of FIG. 2A during inspiration.

FIG. 10A illustrates a novel valve structure with a standoff, with no airflow.

DETAILED DESCRIPTION OF EXAMPLE EMBODIMENTS

Figure 1A:
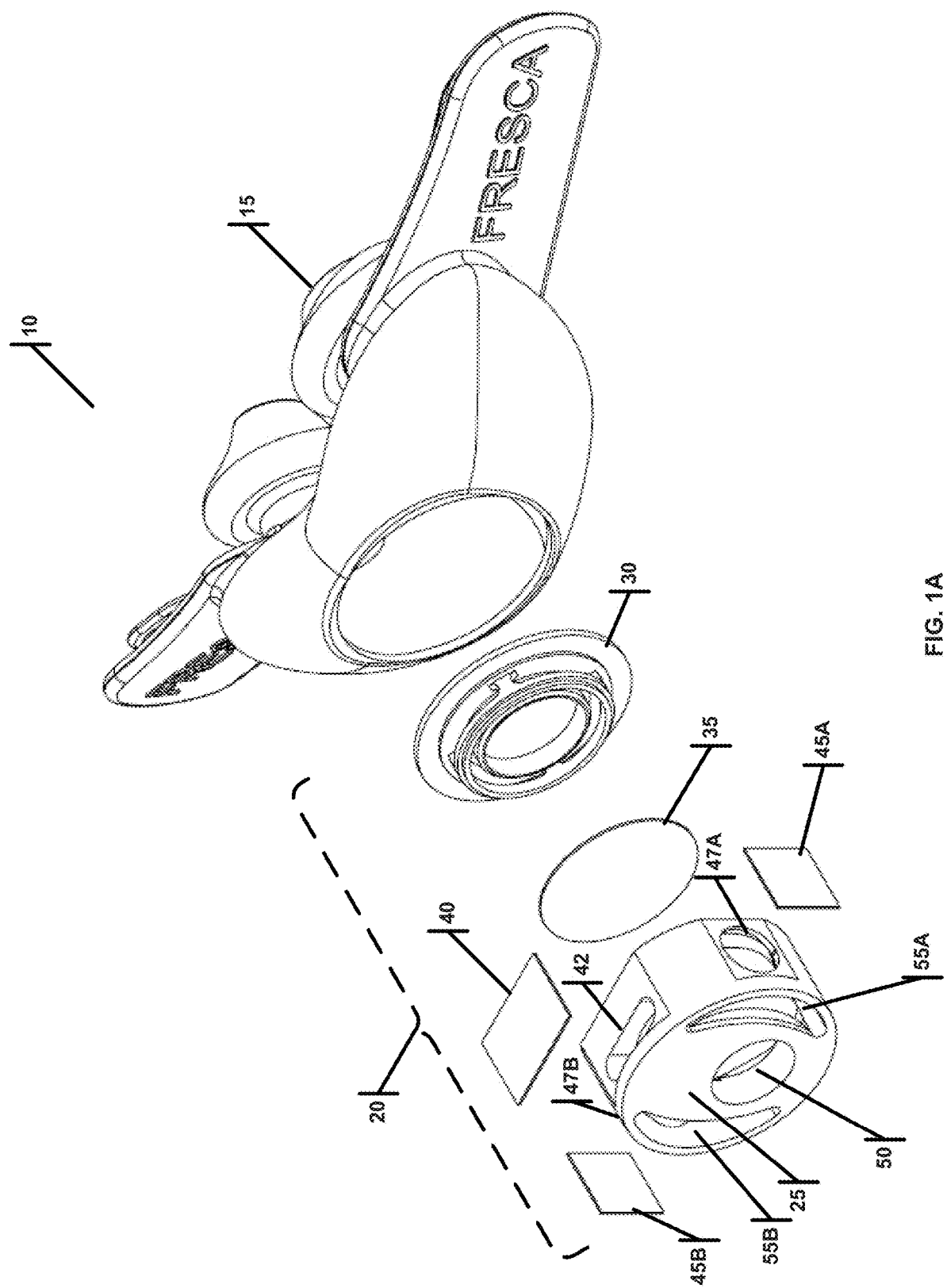
FIG. 1A is an exploded perspective view of an example PAP apparatus according to various example embodiments.
Figure 1B:
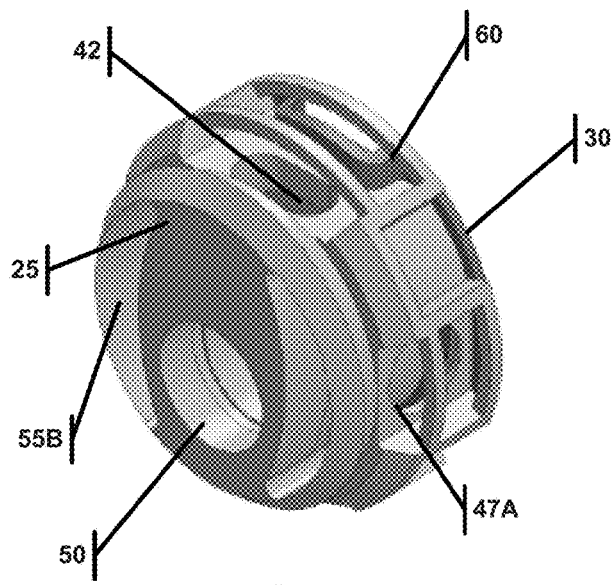
FIG. 1B is a front perspective view of an example valve cartridge adapted for use with the example PAP apparatus of FIG. 1A, according to various example embodiments.
Figure 1C:
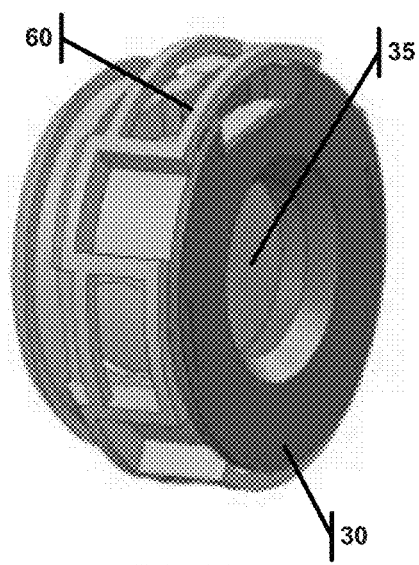
FIG. 1C is a rear perspective view of the example valve cartridge of FIG. 1B according to various example embodiments.
Figure 1D:
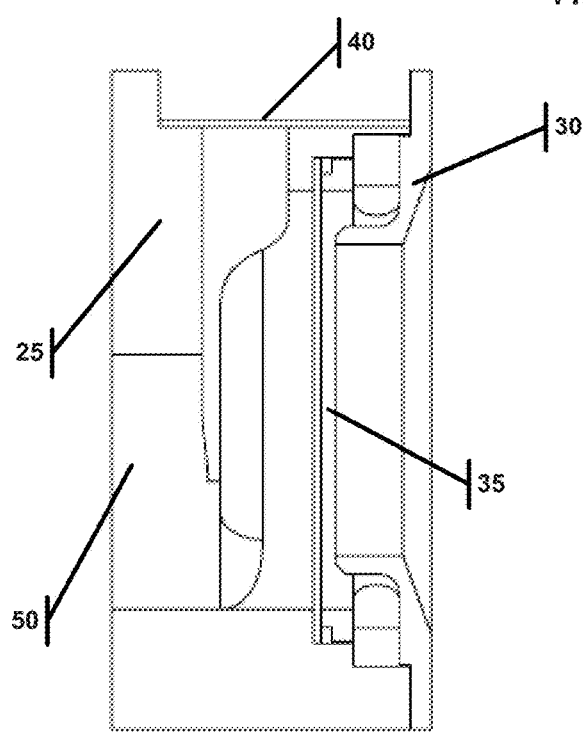
FIG. 1D is a sectional side view taken through the middle of the example valve cartridge of FIG. 1B according to various example embodiments.
Figure 1F:
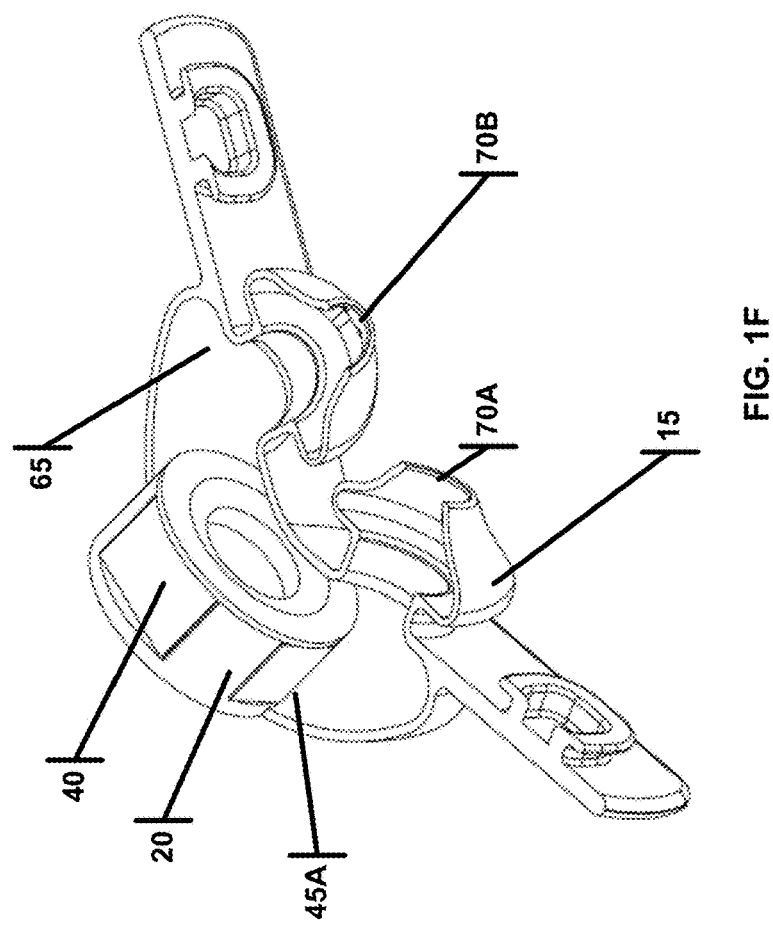
FIG. 1F is a rear perspective sectional view of the example PAP apparatus of FIG. 1A, according to various example embodiments.
Figure 1E:
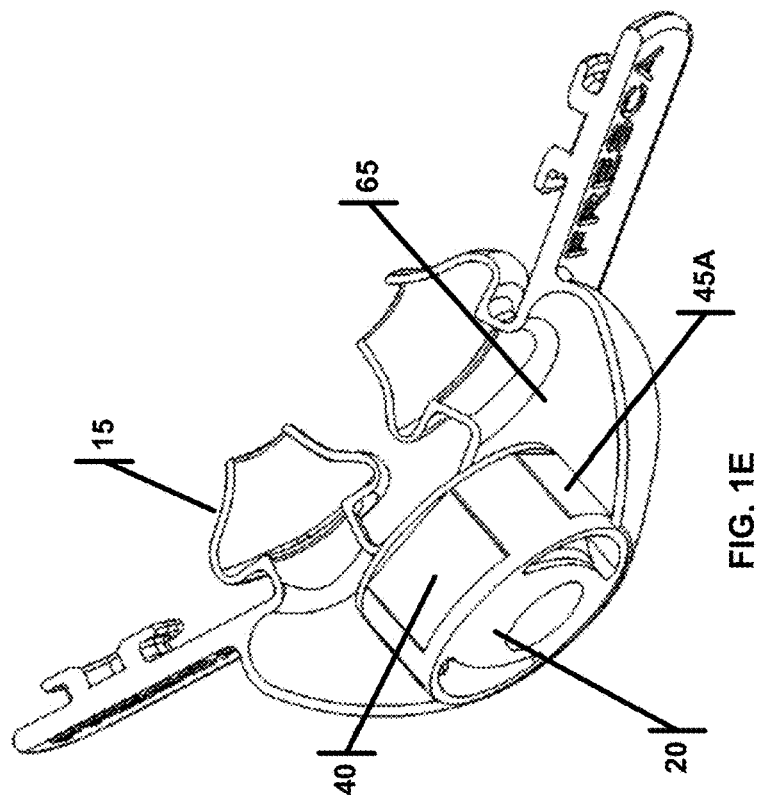
FIG. 1E is a front perspective sectional view of the example PAP apparatus of FIG. 1A, according to various example embodiments.

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents, as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms unless noted otherwise. Similarly, various steps of the methods shown and described herein are not necessarily performed in the order indicated, or performed at all in certain embodiments. Accordingly, some implementations of the methods discussed herein may include more or fewer steps than those shown or described.

Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection, unless otherwise noted.

The following list of example features corresponds with FIGS. 1A-13 and is provided for ease of reference, where like reference numerals designate corresponding features throughout the specification and figures:

Sleep Mask 10
Nasal Pillow 15
Sleep Mask Valve Structure/Cartridge 20
Valve Housing 25
Expiratory Valve Seat 30
Expiratory Valve Membrane 35
Inlet pressure one-way valve Membrane 40
Inlet pressure one-way valve seat 42
Inspiratory one-way valve membranes 45A, B
Inspiratory one-way valve seat 47A, B
Inlet pressure port 50
Ambient Pressure Ports 55A, B
Valve Body connection structure 60
Cavity 65
Compliant/malleable nasal seat 70A, B
Positive pressure 75
Inspiration ambient air stream 80
Inspiration nasal air stream 85
Inspiration positive pressure air stream 90
Inspiration cavity pressure 93
Expiration nasal air stream 95
Expiration ambient air stream 100
Expiration positive pressure air stream 105
Expiration cavity pressure 106
Apnea positive pressure air stream 107
Apnea nasal air stream 108
Apnea cavity pressure 109
Sleep Mask 110
Sleep Mask Valve Structure/Cartridge 115
Sleep Mask Valve Structure/Cartridge Improved Design 115A
Inlet Pressure Port 116
Ambient Pressure Port 117
Valve Housing 120
Valve Housing center Axis 120A
Inspiratory Valve Seat 122
Second Inspiratory Valve Seat 122A
Inlet Pressure Valve Seat 122B
Second Inlet Pressure Valve Seat 122C
Expiratory Valve Seat 123
Expiratory Valve Membrane 125
Expiratory Valve Retaining Seat 130
Inspiratory Valve Retailing Seat 135
Inspiratory Membrane 140
First Segmented Portion of Inspiratory Membrane 140A
Second Segmented Portion of Inspiratory Membrane 140B
Third Segmented Portion of Inspiratory Membrane 140C
Fourth Segmented Portion of Inspiratory Membrane 140D
Retaining Clip 141
Intra-mask Side 142
Outside-mask Side 143
Outer Mask Baffling Screen 150

Intra-mask Baffling Screen 155
Inhaled Fresh Air 160
Blower Air 165
Patient Exhaled Breath 170
Blower Box 180
Tube 185
Non-positive pressure inspiration nasal air flow 220
Non-positive pressure inspiration ambient air flow 230
Non-positive pressure expiration nasal air flow 240
Non-positive pressure expiration ambient air flow 250
Apnea region 260
Valve Structure with Standoff 305
Standoff 310
Secondary Valve Seat 320
Inspiratory Valves 330
Pressurized Inspiratory Valve 340
Expiratory Membrane 350
Pressurized Air From Blower 360
Primary Valve Seat 370.
Pressurized Air From Patient 375
Small Opening/Intended Leak 385
Pressurize Air Flow Path From Blower 390
Air Flow Generator 400
Controller 410
Delay Circuit 420
Initiation Control 440
Transceiver 450
Sleep Detector 460
Conventional positive operation region 465
Positive air pressure of zero while user is falling asleep 470
Operation region of sleep apnea device 475
Increase of positive air pressure after the user falls asleep 480

FIGS. 1A through 1O provide a first embodiment of a sleep mask 10, comprising a unitary nasal pillow 15 configured to be connected to a source of pressurized air, such as a conventional PAP blower box (not shown) via a small-diameter single-lumen hose (now shown). The nasal pillow 15 may be configured to be sealably affixed to the nostrils of a user with compliant/malleable nasal seats 70A, 70B (FIG. 4A) and held in place by adjustable headgear (not shown). The nasal pillow 15 may be formed from any appropriate material, such as silicone.

The nasal pillow 15 may be configured to removably receive therein a centrally-located sleep mask valve structure/cartridge 20, for instance partially or entirely within a sealed internal cavity 65 of nasal pillow 15 (FIGS. 1E, 1F), such that the valve cartridge is removably located almost entirely or entirely inside the exterior profile of the nasal pillow. The sleep mask valve structure/cartridge 20 may in various example embodiments be a unitary cylindrical assembly comprising a valve housing 25 defining an inlet pressure port 50 configured to removably attach with the hose (not shown) communicating pressured air 90 from the PAP blower box (not shown). The valve housing 25 may further define ambient pressure ports 55A, 55B, which may be crescent-shaped and located adjacent and on opposite sides of inlet pressure port 50. The ambient pressure ports 55A, 55B may be configured to be in communication with ambient air 80 in the room where the sleep mask 10 is being used.

One or more flexible expiratory valve membranes 35 (e.g., a distensible or morphable soft membrane, such as a thin sheet of 10 Shore A silicone) may be removably assembled between the valve housing 25 and one or more mating expiratory valve seats 30, for instance by a valve body connection structure 60 (such as a compression-fit or snap-together mechanism 60), such that, while in use, each valve membrane 35 is exposed on one side (distal expiratory valve seat 30) to pressured air 90 communicated through inlet pressure port 50, and is exposed on the opposite side (proximate expiratory valve seat 30) to the expiration nasal air stream 95. Expiratory valve membranes 35 may be formed from a distensible or morphable soft membrane, such as a thin sheet of 10 Shore A silicone, which creates a quiet, effective, and robust seal that tends to effectuate a seal even in the presence of minor debris, lint, and residue.

The valve housing 25 may further comprise one or more inlet pressure one-way valve membranes 40 that, while in use, are exposed on one side to pressured air 90 communicated through inlet pressure port 50, and are exposed on the opposite side to expiration nasal air stream 95. One-way valve membranes 40 may be configured to open and allow pressured air 90 to flow from inlet pressure port 50 into cavity 65 of nasal pillow 15 when pressured air 90 is at a higher pressure than the expiration nasal air stream 95. Conversely, one-way valve membranes 40 may be configured to close and seal against the inlet pressure one-way valve seat 42 formed in the valve housing body 25 to prevent air flow between inlet pressure port 50 and cavity 65 when pressured air 90 is not at a higher pressure than the expiration nasal air stream 95.

Valve housing 25 may also comprise one or more inspiratory one-way valve membranes 45A, 45B, configured such that in use each inspiratory one-way valve membrane 45A, 45B is exposed on one side to ambient air 80 communicated through ambient pressure ports 55A, 55B, respectively, and is exposed on the opposite side to the expiration nasal air stream 95. Inspiratory one-way valve membranes 45A, 45B may be configured to open and allow ambient air 80 to flow from ambient pressure ports 55A, 55B, respectively, into cavity 65 of nasal pillow 15 when ambient air 80 is at a higher pressure than the expiration nasal air stream 95. Conversely, inspiratory one-way valve membranes 45A, 35B may be configured to close and seal against inspiratory one-way valve seats 47A, 47B, formed in valve housing 25 to prevent air flow between the ambient pressure ports 55A, 55B and the cavity 65 when ambient air 80 is not at a higher pressure than the expiration nasal air stream 95. The expiratory valve (formed by expiratory valve membrane 35 and expiratory valve seat 30) and inspiratory valves (formed by inspiratory one-way valve membrane 45A, 45B and inspiratory one-way valve seat 47A, B) share the same ambient pressure ports 55A, 55B, such that the device is simple to manufacture and easy for the user to clean. Also, the example design shown in the figures includes no dead-end cavities or difficult-to-access recesses in the air flow channels, which allows a user to clean and dry the device effectively without leaving moisture that might breed mold or mildew.

An example sleep mask 10 will now be described in use as part of a system, according to various example embodiments. The nasal pillow 15 may be connected with a traditional PAP blower box (not shown) via a hose (not shown). The nasal pillow 15 may be affixed to the nostrils of a user (not shown) via a silicone or similar nasal interface 70A, 70B, and adjustable headgear (not shown). The function of the nasal pillow 15 may be described by three distinct modes: inspiration, expiration, and rest/apnea, depicted in FIGS. 4A, 4B, 5, respectively (where only one inspiratory one-way valve membrane and seat are shown) and again at FIGS. 1G-1I, 1J-1L, and 1M-1O respectively (where two inspiratory one-way valve membranes and seats are shown).

Figure 2A:
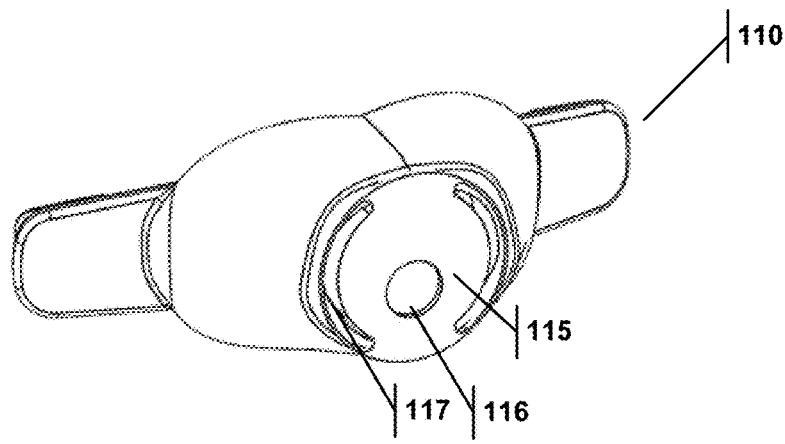
FIG. 2A illustrates a second embodiment of a novel sleep mask and valve structure for use in the treatment of sleep apnea.
Figure 2B:
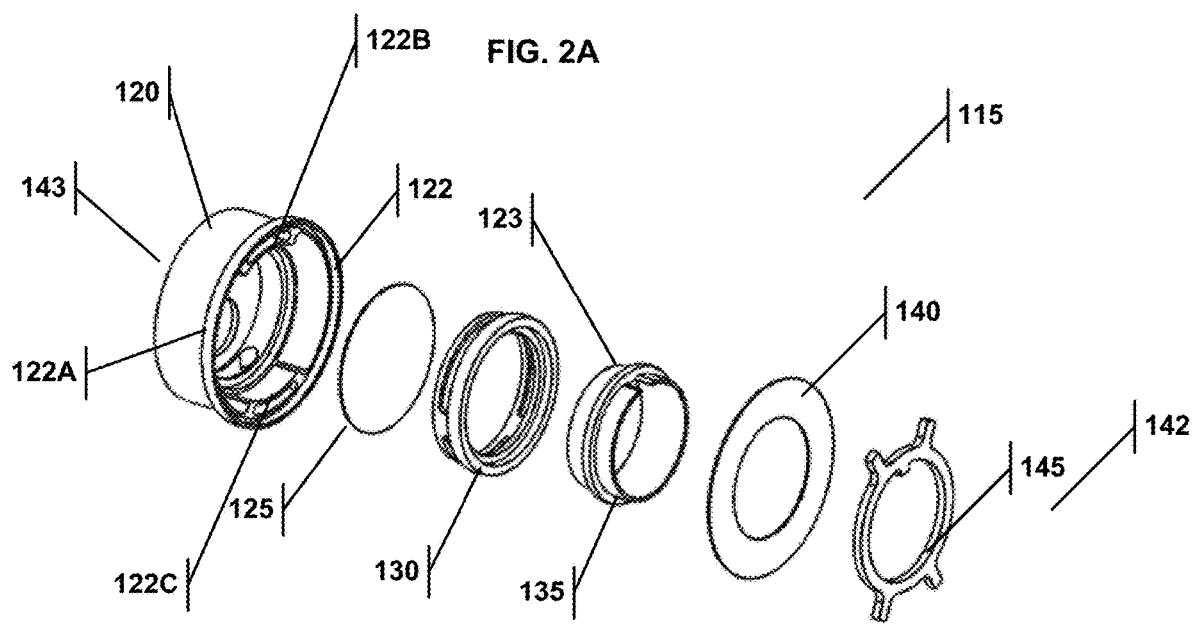
FIG. 2B illustrates in an exploded view of the various parts of the novel valve structure of FIG. 2A.
Figure 2B:
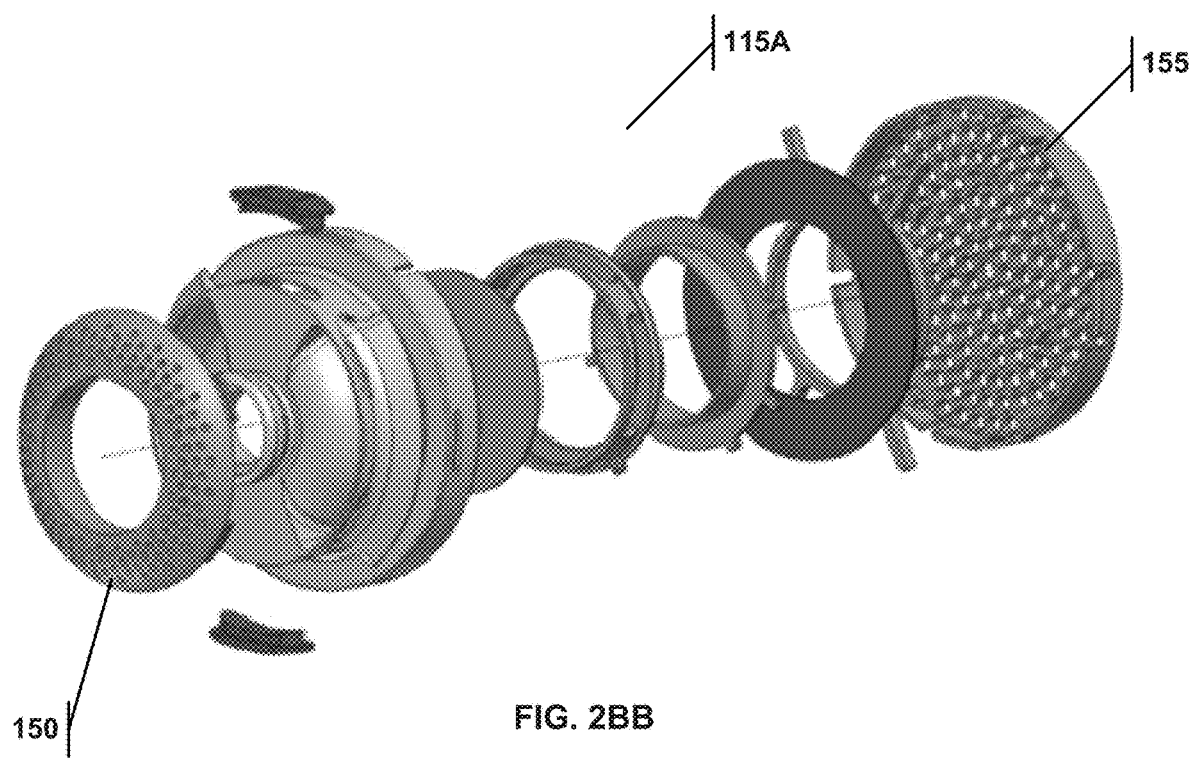
Figure 2J:
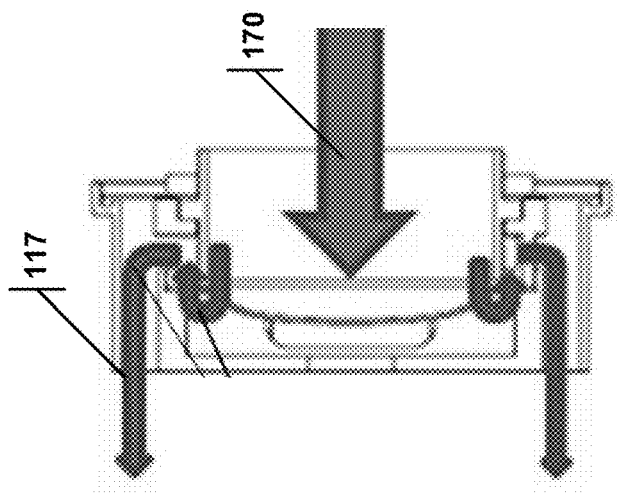
FIG. 2J shows the exhaled breath air flow of the novel valve structure of FIG. 2A during expiration.
Figure 2I:
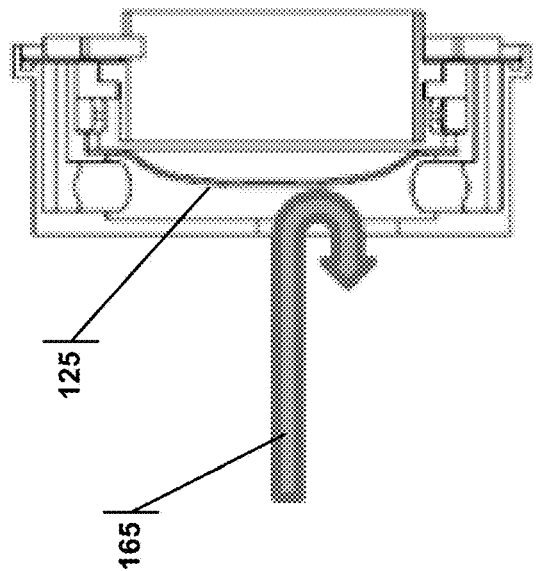
FIG. 2I shows the blower air flow of the novel valve structure of FIG. 2A during expiration.
Figure 2G:
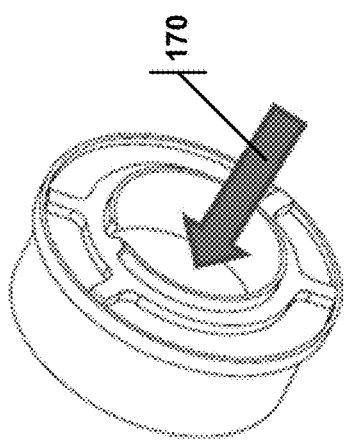
FIG. 2G shows the exhaled breath air flow of the novel valve structure of FIG. 2A during expiration.
Figure 2H:
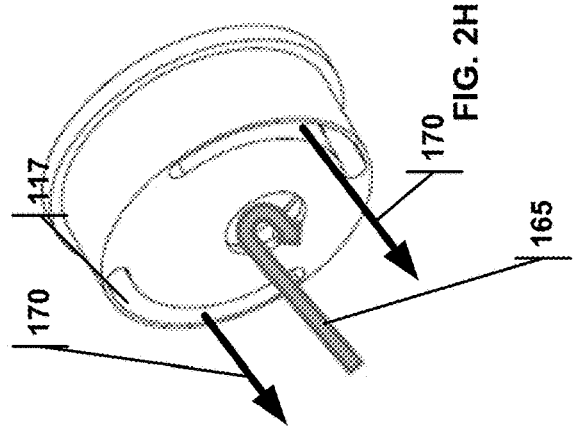
FIG. 2H shows the blower air flow of the novel valve structure of FIG. 2A during expiration.

A second embodiment is shown in FIGS. 2A and 2B. The sleep mask 110 contains a sleep mask valve structure/cartridge 115 that is comprised of a ridge or semi-rigid valve housing 120, expiratory valve membrane 125, an expiratory valve retaining seat 130, and inspiratory valve seat 125, an inspiratory valve membrane 140 and a retaining clip 145. The inspiratory valve membrane 140 and expiratory valve membrane may be formed from a sound absorbing material, such as an elastomer. To further mitigate sound, the valve housing 120 may include a sound absorbing liner, made of a material with a preferred durometer of 50A to 90A.

The valve housing 120 also forms an inspiratory valve seat 122 that, in combination with the inspiratory valve membrane 140, creates a one-way valve. Further, the valve has an inlet pressure valve seat 122B that uses the same inspiratory valve membrane 140, creating a one-way valve inlet pressure valve, but the membrane action is segmented by use of the retaining clip 145. The valve housing 120 also forms an expiratory valve seat 123 that forms a variable resistance expiratory valve, which can be adjusted based on the pressure of the blower air. The sleep mask valve structure/cartridge 115 has an intra-mask side 142 that is proximal (as a function of air path) to the patient and an outside-mask side 143 that is distal to the patient.

Pressurized air is delivered to the valve structure/cartridge 115 through the inlet pressure port 116. Air exhausted through expiration or inhaled through inspiration may travel through the ambient pressure port 117.

The operation of this sleep mask valve structure/cartridge 115 is shown in FIGS. 2C-2L. Specifically, FIGS. 2C-2F illustrate the inspiration mode and in particular the flow paths of the inhaled fresh air 160 and the blower air 165. The fresh air 160 moves into the valve structure/cartridge 115 through the ambient pressure port 117 and unseats the inspiratory membrane 140 from the inspiratory valve seat 122, allowing fresh air 160 to enter the mask. The blower air 160 moves into the valve structure/cartridge 115 through the inlet pressure port 116 and unseats the inspiratory membrane 140 from the inlet pressure valve seat 122B, allowing blower air 160 to enter the mask (see FIG. 2C). The retaining clip 145 segments the action of the inspiratory membrane 140, forming two inspiratory valves and two inlet pressure valves. The valve structure/cartridge 115 and housing 120 therefore define inspiratory airflow conduit (shown by the airflow movement arrows in FIGS. 2C-2F), accommodating airflow from the outside mask side 143 to the intra-mask side 142. This dual-purpose use of the inspiratory membrane 140 allows for fewer parts in the final construction, easing manufacturing and reducing costs.

FIG. 2G-2J illustrates the expiration mode and the flow paths of the blower air 165 and the patient's exhaled breath 170. In the expiration mode, the blower air 165 applies a pressure against the expiratory valve membrane 125. This resistance can assist in preventing an apnea event. The valve structure/cartridge 115 and the housing 120, therefore, define the expiratory airflow conduit (shown by the exhaled breath 170 in FIGS. 2G-2J), accommodating airflow from the intra-mask side 142 to the outside mask side 143. The exhaled breath 170 exits the valve structure/cartridge 115 through the ambient pressure port 117.

Figure 2L:
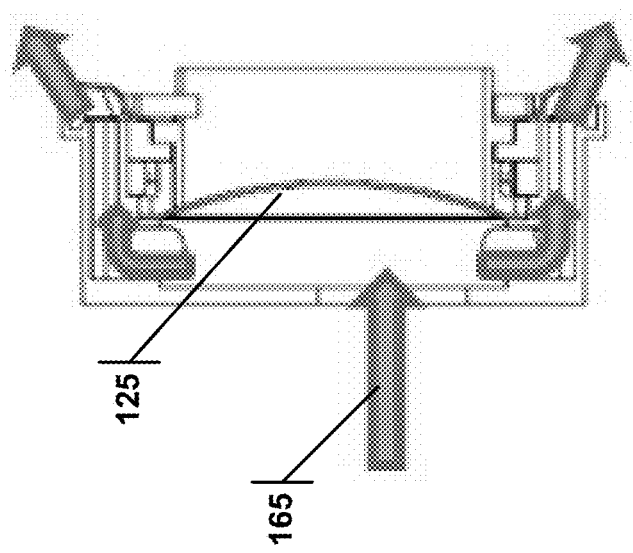
FIG. 2L shows the blower air flow of the novel valve structure of FIG. 2A during apnea.
Figure 2K:
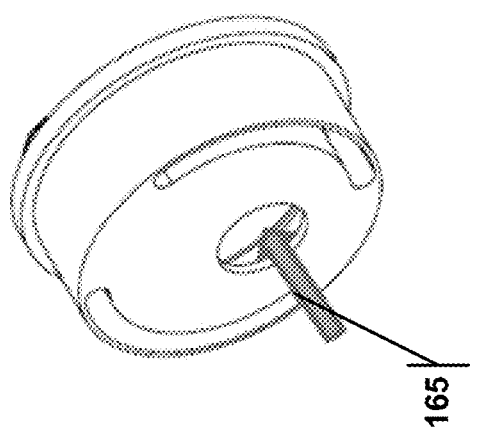
FIG. 2K shows the blower air flow of the novel valve structure of FIG. 2A during apnea.

FIGS. 2K-2L illustrate the apnea mode of the valve structure, with the blower air 165 applying a pressure against the expiratory valve membrane 125 while simultaneously providing a positive pressure of air to the patient, thus offering a therapeutic pneumatic splint that maintains the patient's airway open preventing an apnea event.

Figure 2M:
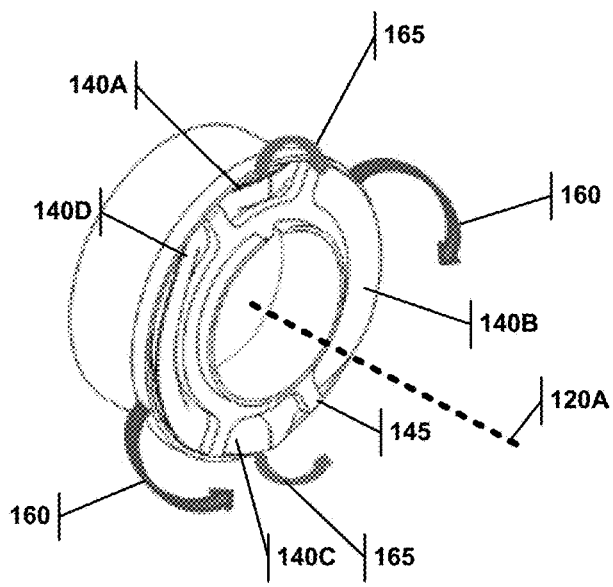
FIG. 2M shows the fresh air flow and the blower air flow of the novel valve structure of FIG. 2A during inspiration.
Figure 2N:
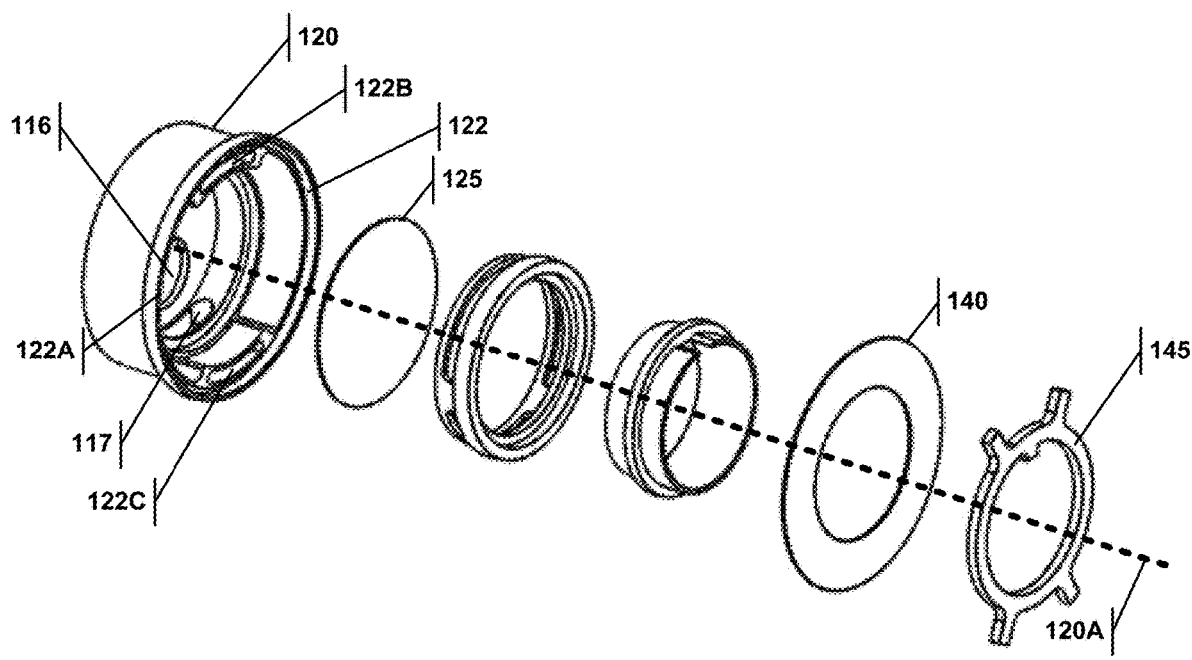
FIG. 2N illustrates in an exploded view the various parts of the novel valve structure of FIG. 2A.

FIGS. 2M and 2N illustrate the simplicity of the radial design that uses a single inspiratory membrane 140 with a clip 145 that acts as inspiratory membrane segmentation structure that segments the movement of the inspiratory membrane 140. Specifically, the clip 145 segments the movement into a first portion 140A, a second portion 140B, a third portion 140C and a fourth portion 140D. The valve housing 120 has an inlet pressure port 116 and an ambient pressure port 117. Within the housing 120 is the expiratory membrane 125, an expiratory valve seat 123, an inspiratory membrane 140, an inlet pressure valve seat 122B, an inspiratory valve seat 122, and the clip 145 (i.e., an inspiratory membrane segmentation structure configured to segment the movement of the inspiratory membrane). An expiratory valve in fluid connection with the inlet pressure port is formed by the expiratory membrane 125 and the expiratory valve seat 123. An inlet pressure valve is formed by the inlet pressure valve seat 122B and the first portion of the inspiratory membrane 140A. The inlet pressure valve is constructed to allow air flow 165 from the inlet pressure port 116 (connected to the blower) into the mask with little resistance and block air flow from within the mask out. An inspiratory valve is formed by the inspiratory valve seat 122 and the second portion of the inspiratory membrane 140B. The inspiratory valve is constructed to allow air flow from the ambient pressure port 117 into the mask with little resistance and block air flow from within the mask out. A second inlet pressure valve is formed by the second inlet pressure valve seat 122C and the third portion of the inspiratory membrane 140C. A second inspiratory valve is formed by the second inspiratory valve seat 122A, and the fourth portion of the inspiratory membrane 140D. As shown in FIG. 2N, the inspiratory valve seats 122, 122A and the inlet pressure valve seats 122B, 122C can be integrally formed in the housing 120. The housing 120 may define a housing center axis 120A. The expiratory membrane 125 is substantially planar and may be oriented substantially orthogonal to the housing center axis 120A. Likewise, the inspiratory membrane 140 is substantially planar and may be oriented substantially orthogonal to the housing center axis.

The expiratory membrane 125 may define an expiratory membrane center axis that is orthogonal to the plane defined by the expiratory membrane 125 and is substantially coincident with the housing center axis 120A. Likewise, the inspiratory membrane 140 may define an inspiratory membrane center axis that is orthogonal to the plane defined by the inspiratory membrane 145 and is substantially coincident with the housing center axis 120A.

Figure 3:
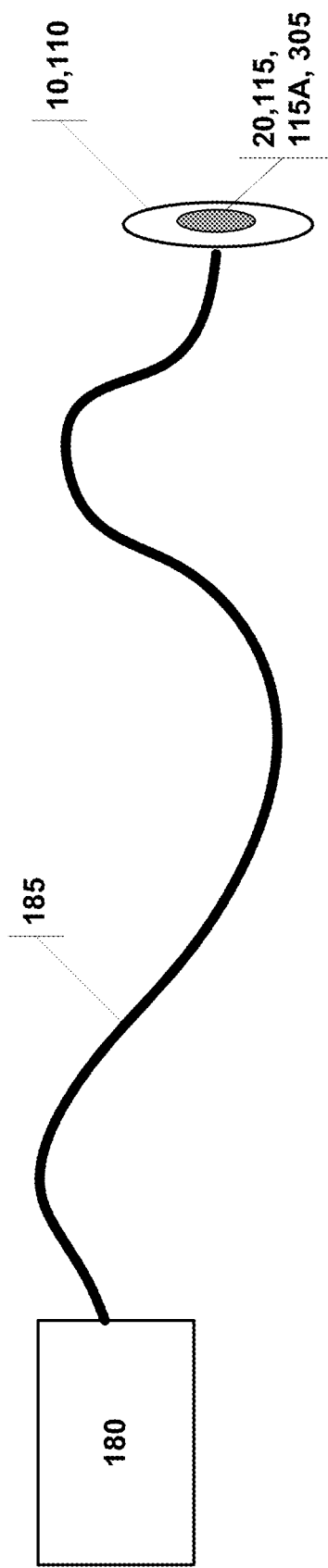
FIG. 3 illustrates the valve structures used as part of a larger system for treating a patient suffering from obstructive sleep apnea.

FIG. 3 illustrates the valve structures used as part of a larger system, which includes a blower box 180, a tube 185 connected to a mask (10, 110). The unique design of the valve structures discussed herein allows the supplied air and the valve controlling air to be combined into a single hose with a single lumen. This has unique advantages, in that the hose can be smaller, more supple (an important user feature is not having a cumbersome hose to distract from sleeping), easier to clean (the system need not have any elongated, small lumens that end in a closed compartment in the valve resistance generating chamber), and easier to connect as only a single orientation independent hub is needed at either end. For example, an outer diameter of the hose can be between about 3.0 mm and about 15.0 mm. In some embodiments, an inner diameter of those hoses can be less than or equal to about 10.0 mm, e.g., between about 5.0 mm and about 10.0 mm. In some embodiments, a wall thickness of those hoses can be less than or equal to about 1.0 mm, e.g., between about 0.5 mm and about 0.75 mm. The smaller hose is less bulky than traditional hoses for CPAP devices. Such a hose is described in U.S. patent application Ser. No. 14/278,587 filed on May 15, 2014, 62/246,477 filed on Oct. 26, 2015 and 62/694,126 filed on Jul. 5, 2018, the contents of which are incorporated by reference in their entireties.

In various example embodiments discussed, the valve structure/cartridge may have three modes: inspiration, expiration and rest/apnea. In operation, the valve structure is connected to a mask and properly affixed to a patient. The blower box is set to the user's prescribed pressure, e.g., 0-20 cmH$_2$O. The blower box may immediately apply this pressure, or as discussed below the pressure may be delayed and graduated.

The device mode of "inspiration" starts when the user inhales, as depicted in FIGS. 4A, 1G-1I and 2C-2F. As the user inhales, inlet pressure one-way valve membrane (40, 140) and inspiratory one-way valve membranes (45A, 45B, 140) open and both ambient room air (80,160) and pressurized blower air (90,165) enter the mask at an inspiration cavity pressure 93, and that air flows through nasal interface 70A, 70B to the user as inspiration nasal air stream 85. Inspiration also causes the pressurized blower air (90, 165) to create a net positive pressure 75 over the expiratory valve membrane (35, 125), causing it to sealably close against the expiratory valve seat (30, 123). Since the expiratory valve membrane (35, 125), may be formed from a soft, flexible, compliant material, it advantageously makes little to no noise when it moves and engages and disengages the valve seat (30, 123). This helps the user go to sleep and increases effectiveness by increasing user compliance with usage regimens.

Figure 4A:
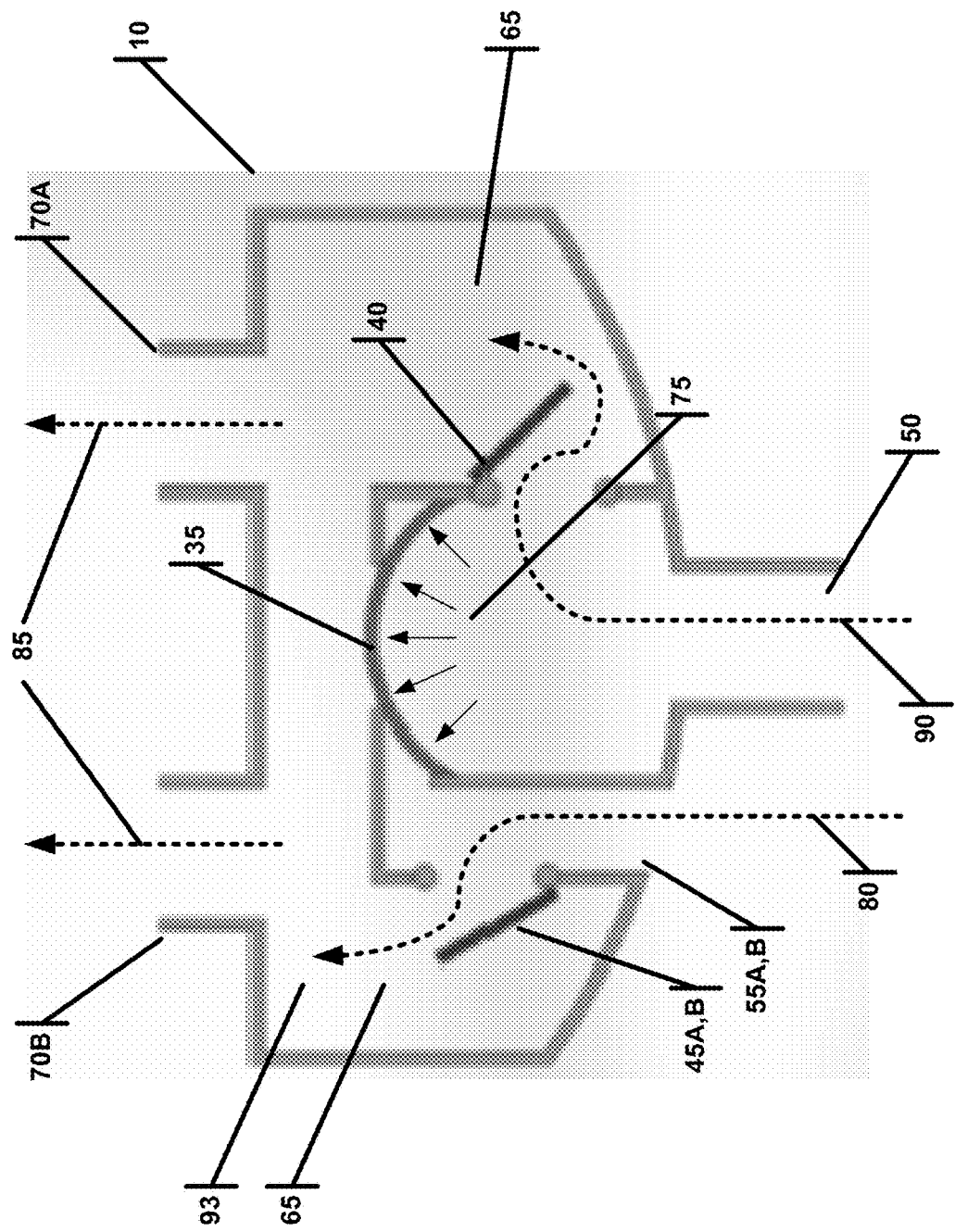
FIG. 4A is a schematic functionally depicting various aspects of an example PAP apparatus operating during the inspiration mode, according to various example embodiments.
Figure 4B:
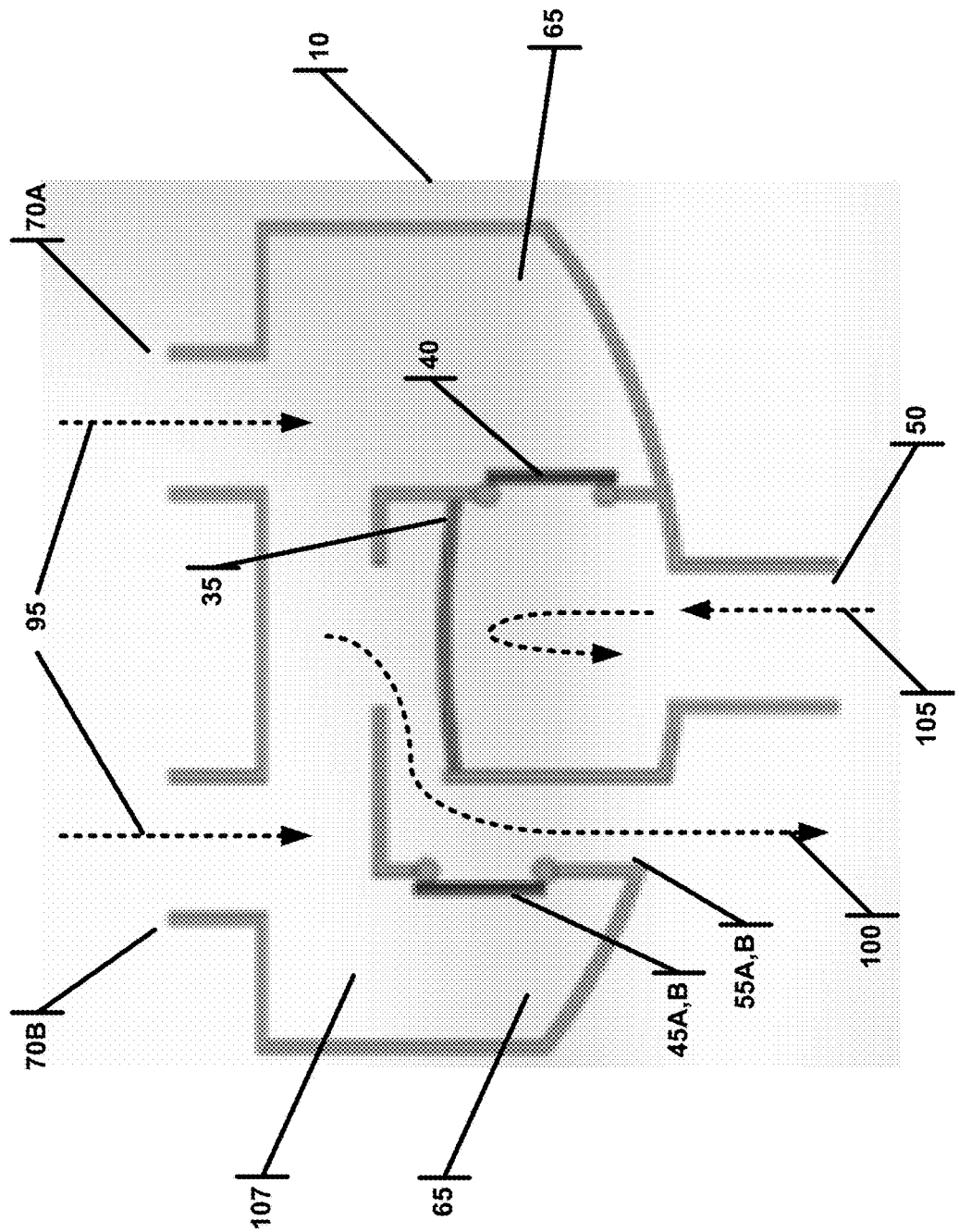
FIG. 4B is a schematic functionally depicting various aspects of an example PAP apparatus operating during the expiration mode, according to various example embodiments.
Figure 5:
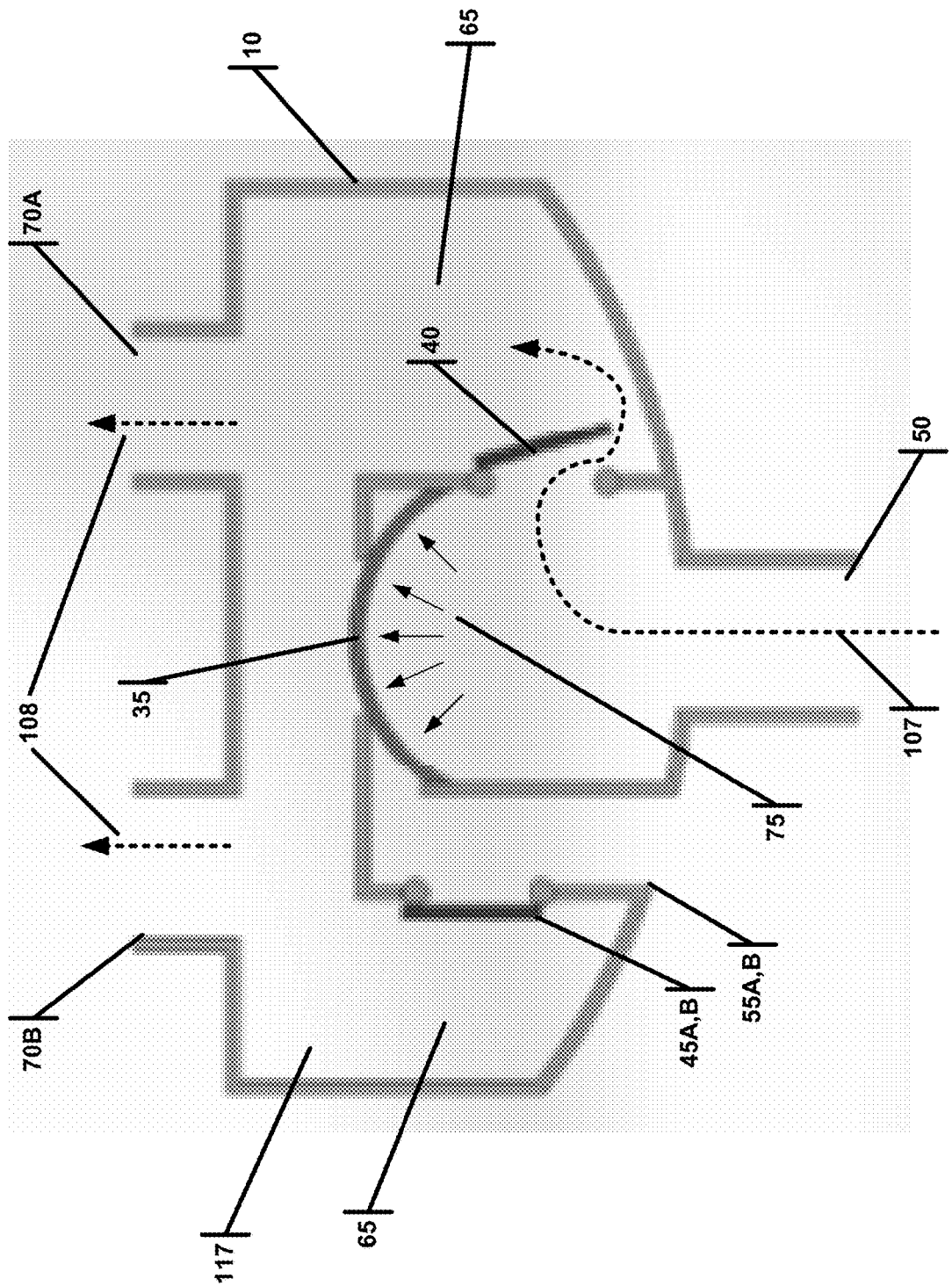
FIG. 5 is a schematic functionally depicting various aspects of an example PAP apparatus operating during the rest/apnea mode, according to various example embodiments.
Figure 6A:
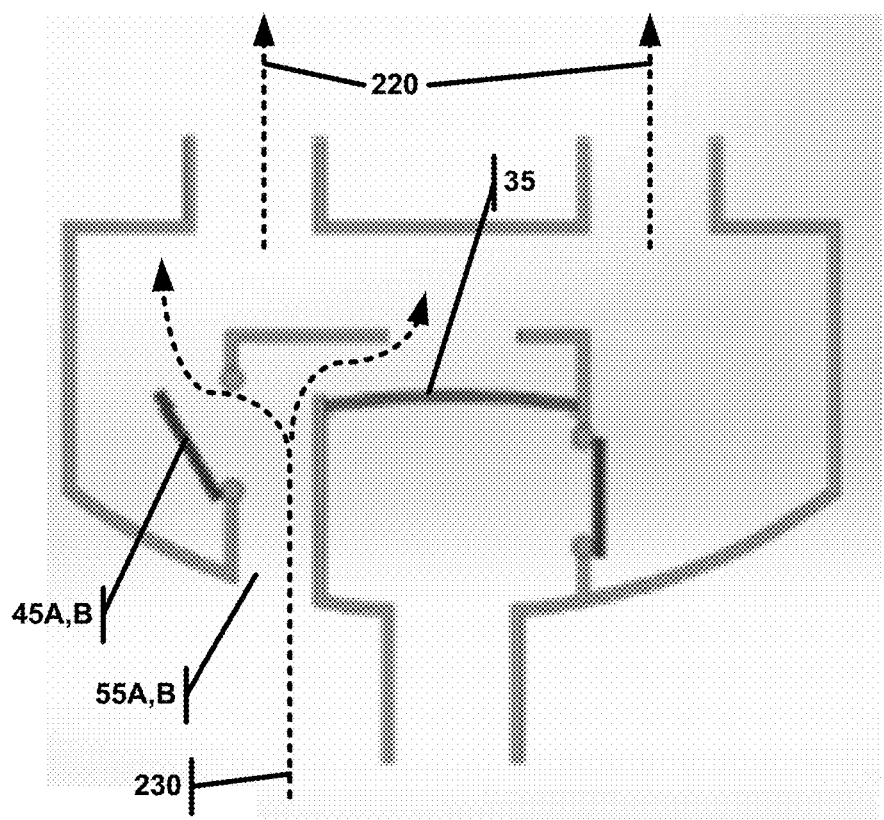
FIG. 6A is a schematic functionally depicting various aspects of an example PAP apparatus during inspiration when the blower is off (disconnect mode), according to various example embodiments.
Figure 6B:
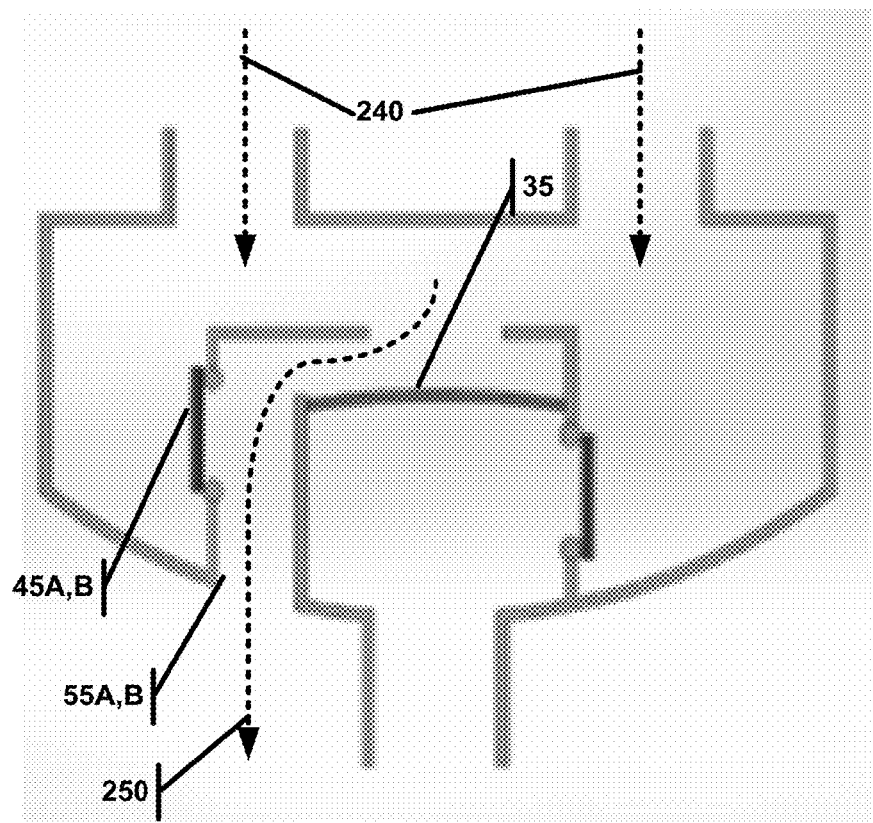
FIG. 6B is a schematic functionally depicting various aspects of an example PAP apparatus during expiration when the blower is off (disconnect mode), according to various example embodiments.

As depicted in FIG. 4A, the expiratory valve membrane (35, 125) is sealably closed against expiratory valve seat (30, 123) because of a net force differential across the expiratory valve membrane (35, 125) in the direction of positive pressure 75, but only when the expiratory valve membrane (35, 125) is closed against the seat (30, 123), as shown in FIGS. 4B and 5. Once the expiratory valve membrane (35, 125) is closed against the seat (30, 123), this net force differential tends to bias expiratory valve membrane (35, 125) closed against the seat (30, 123) until the pressure in the cavity 65 increases above the pressure of blower air (90, 165), at which time the expiratory valve membrane (35, 125) begins to open and unseats from the seat (30, 123), causing the expiratory valve membrane (35, 125) to open.

After inspiration, the user will begin to exhale. The state of expiration starts when the user exhales, as depicted in FIGS. 4B, 1J-1L and 2G-2J. Exhalation causes the pressure inside the mask to rise up to and slightly higher than the blower box setting, thereby causing the inlet pressure one-way valve membrane (40, 140) and inspiratory one-way valve membranes (45A, 45B, 140) to close. With the inlet pressure one-way valve membrane (40, 140) closed, an expiration positive pressure air stream 105 builds pressure in the inlet pressure port (50, 116). This pressurized air 105 applies a force to the expiratory valve membrane (35, 125), urging it toward the expiratory valve seat (30, 123), and sealing it against the expiratory valve seat (30, 123) until the expiration nasal air stream 95 builds up enough pressure in the cavity 65 to overcome the force of pressurized air 105 and unseat the expiratory valve membrane (35, 125) from the expiratory valve seat 30, thereby permitting the user to exhale, via the open expiration ambient air stream 100 flowing out into the room through ambient pressure ports (55A, 55B, 117). This is how the present system governs the expiration cavity pressure 106; i.e., it is a direct and passive function of the amount of blower pressure 105. Accordingly, a blower set at different pressure settings will pressurize the expiratory valve membrane (35, 125) to different resistances. A lower blower box setting results in a lower resistance to unseating the expiratory valve membrane (35, 125) from expiratory valve seat (30, 123), and thus causes a lower expiration cavity pressure 106. A higher blower box setting results in a higher resistance to unseating the expiratory valve membrane (35, 125) from expiratory valve seat (30, 123), and thus causes a higher expiratory cavity pressure 106. This unitary nasal pillow 15 system can thus automatically and passively react to a multitude of blower box pressure settings. It also is contemplated that the nasal pillow 15 can react to real-time changes in the blower box pressure setting. For example, if the blower box has ramps, pressure relief, or dynamically titrates pressure, the nasal pillow 15 should be able to instantly react appropriately.

If the user is sleeping normally, the user will finish exhalation and will begin a new inhalation breath.

However, if either inspiration or expiration is stopped, for instance by apnea, the nasal pillow 15 will automatically enter into rest/apnea mode as depicted in FIGS. 5, 1M-1O and 2K-2l. In this state the user is neither inhaling nor exhaling, so the expiratory valve membrane (35, 125) is sealably seated against the expiratory valve seat (30, 123) by the apnea positive pressure air stream 107 in the inlet pressure port (50, 116). The apnea positive pressure air stream 107 quickly builds up in the inlet pressure port (50, 116) to a higher pressure than the initial apnea cavity pressure 109 in the cavity 65, causing the inlet pressure one-way valve membrane (40, 140) to open, thereby pressurizing the cavity 65 and causing the inspiratory one-way valve membranes (45A, 45B, 140) to close. Air from the blower 107 then builds up pressure 109 in the interior 65 of the nasal pillow 15 to the pressure set at the blower box. The pressure 109 inside the pillow 15 will then splint the user's airway, and the air from the blower box will flow through the nasal interface 70A, 70B to the user as apnea nasal air stream 108, allowing the user to return to breathing. Notably, only a minimal air flow is required from the hose, just enough to achieve a "dead-headed" pressure of the blower box or a minimal flow necessary to achieve pressure and make up for any small system leaks.

Since the present system is so sensitive and quick-reacting, in certain applications it may be appropriate to use it with a blower or airflow generator that need not run continuously, but rather is only activated as needed, for instance immediately upon detection of OSA. This option is possible with the present system in part because its unique valving system provides the additional feature of allowing a user to breathe normally while wearing it when there is no airflow or pressure being provided to the inlet port (50, 116) by a blower—i.e., the disconnect mode. This is demonstrated in FIGS. 6A and 6B, which show that when there is no airflow or pressure being provided to the inlet port (50, 116) by a blower, the expiratory valve membrane (35, 125) will automatically move to its neutral position, which is unseated from the expiratory valve seat (30, 123), thereby opening a breathing path for the user. Specifically, upon inspiration, non-positive pressure inspiration ambient air flow 230 may travel through ambient pressure ports (55A, 55B, 117), providing the user with non-positive pressure inspiration nasal air flow 220. Further facilitating inspiration, inspiratory one-way valve membranes (45A, 45B, 140) will open upon inhalation, providing increased non-positive pressure inspiration ambient air flow 230 through ambient pressure ports (55A, 55B, 117), thus providing the user with increased non-positive pressure inspiration nasal air flow

220. It is also possible that, depending on the pressure in the cavity and the construction of the expiratory valve membrane (35, 125), that the expiratory valve member (35, 125) may seat with the expiratory valve seat (30, 123) during inhalation; thus, all airflow would travel through the ambient pressure ports (55A, 55B, 117) and through the inspiratory one-way valves. And upon expiration, non-positive pressure expiration ambient air flow 250 may travel past the open expiratory valve membrane (35, 130) and through ambient pressure ports (55A, 55B, 117), providing the user with non-positive pressure expiration nasal air flow 240.

Figure 7A:
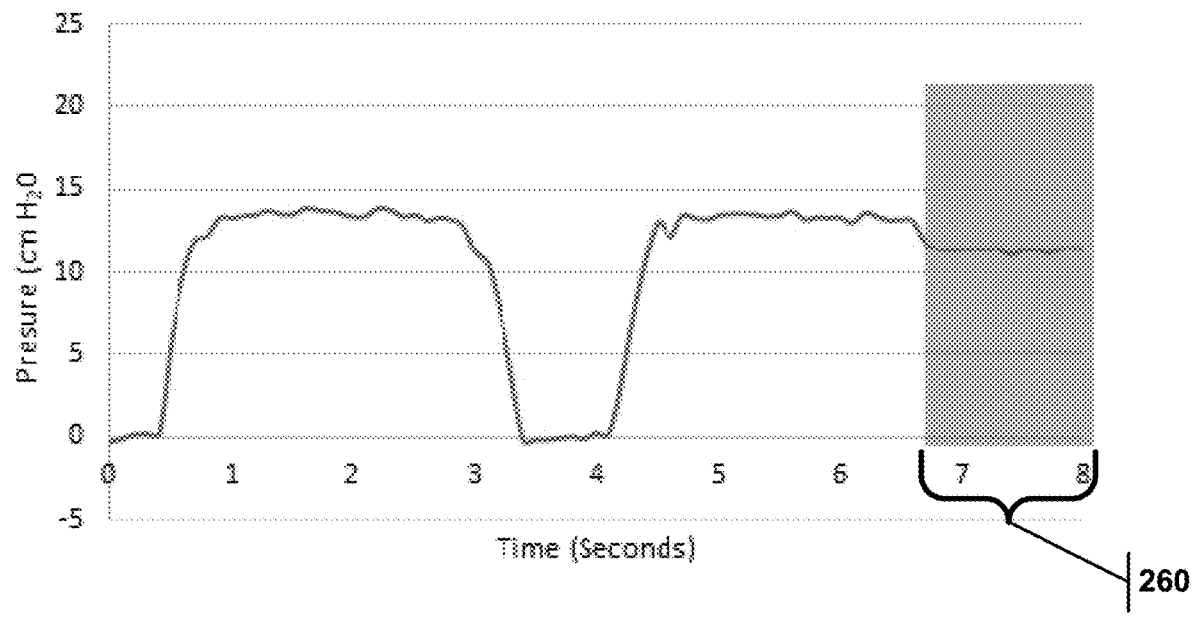
FIG. 7A illustrates the response of the novel valve structure when an apnea event occurs during inspiration.
Figure 7B:
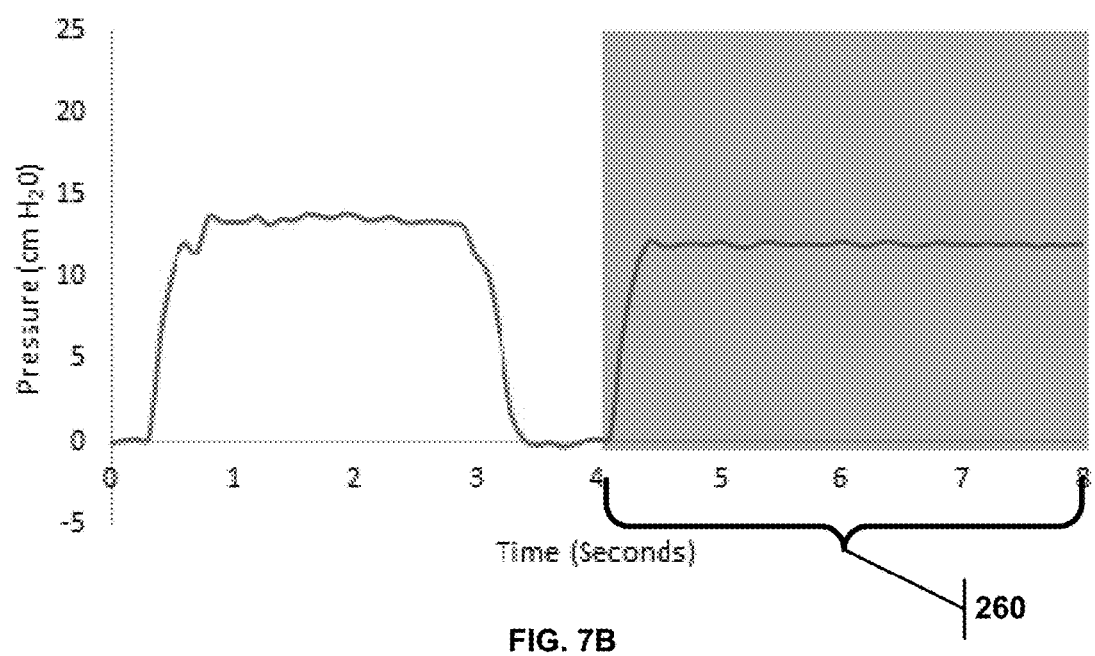
FIG. 7B illustrates the response of the novel valve structure when an apnea event occurs during expiration.
Figure 7C:
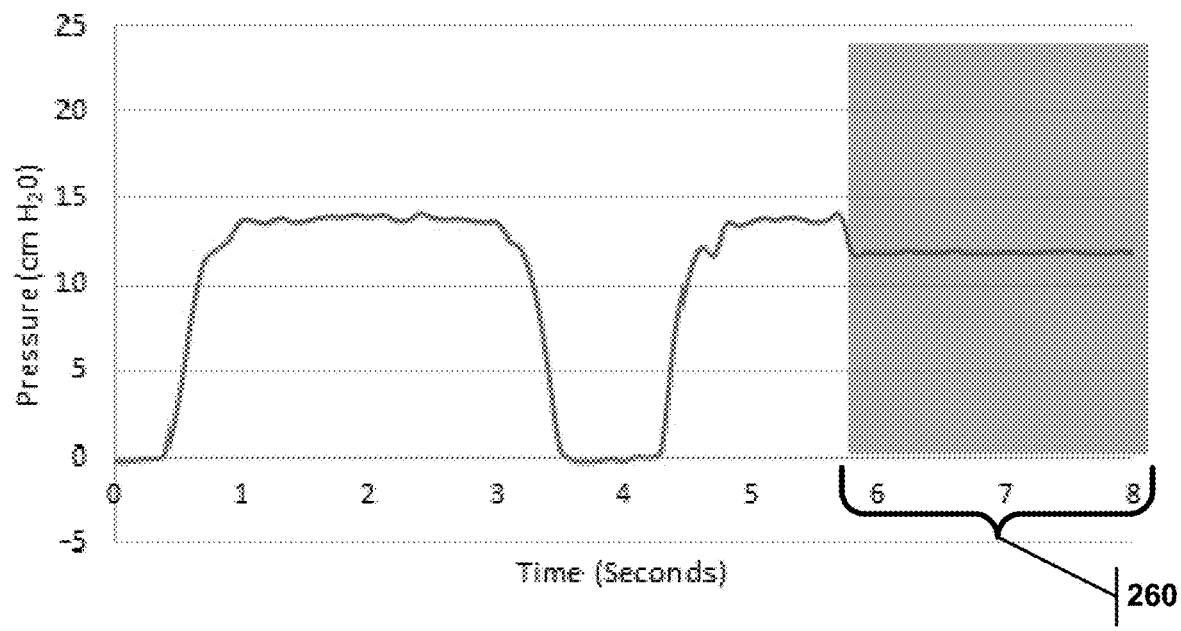
FIG. 7C illustrates the response of the novel valve structure when an apnea event occurs during mid-expiration.
Figure 7D:
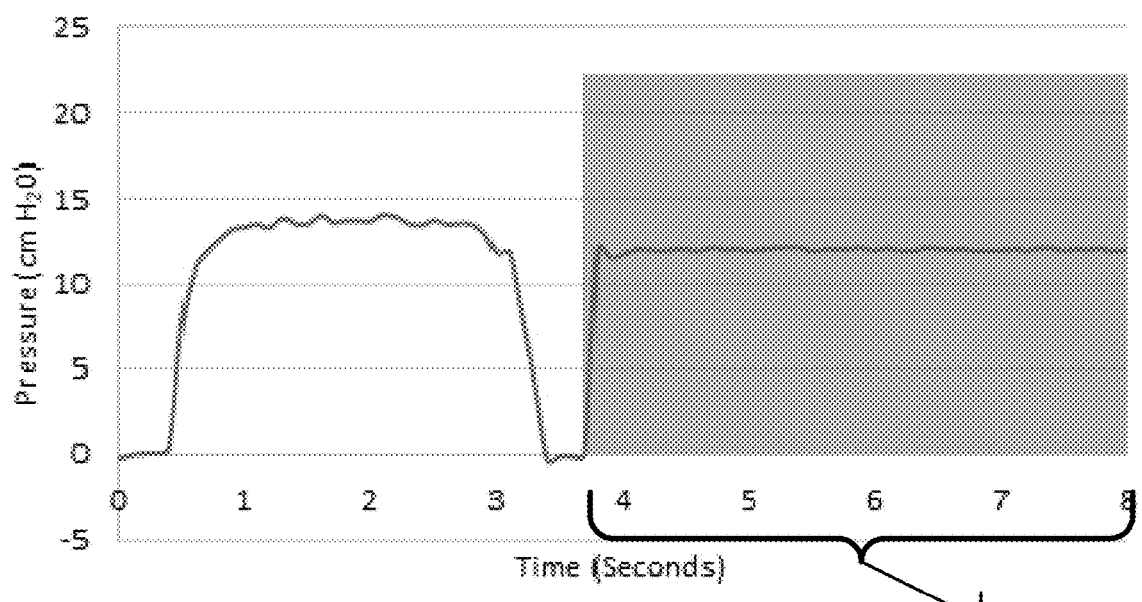
FIG. 7D illustrates the response of the novel valve structure when an apnea event occurs during mid-inspiration.

FIG. 7A captures the pressure response of the valve structures disclosed herein if the cessation of breathing occurs during inspiration, or during a "pause" between inspiration and expiration. The apnea region 260 represents the moment at which the simulated apnea begins. Likewise, FIGS. 7B, 7C and 7D capture the pressure response for an apnea event during expiration, mid-expiration and mid-inspiration, respectively.

FIGS. 7A-7D illustrate the valve response to incipient apnea at various stages of the breathing cycle. In these simulations, the flow generator pressure was set to 12 cmH$_2$O and the respirator was set to 500 cc tidal volume at 15 breaths per minute with an inspiratory: expiratory ratio of 1:3. These figures confirm that the system response is immediate and not dependent on the precise point within the respiratory cycle that an apnea occurs. Within less than a second, more precisely within less than a quarter of a second (shown most clearly in FIGS. 7B and 7D), the valve structures can reach therapeutic pressure from ambient pressure. And again, the valves can reach this pressure, regardless of when in the breathing cycle the apnea event occurs.

Figure 8:
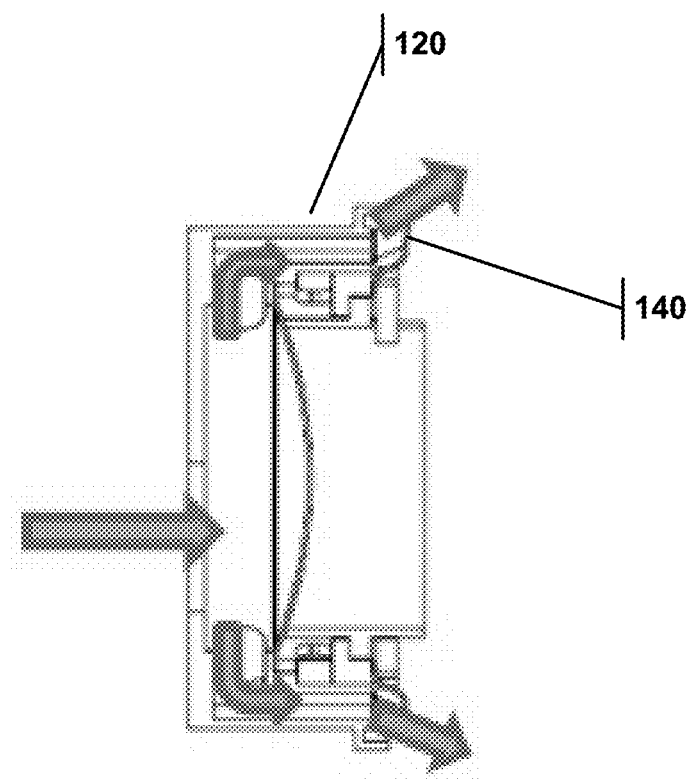
FIG. 8 illustrates the flow path in the novel valve structure during an apnea event.

The testing shown in FIGS. 7A-7D was performed on the second embodiment valve structure (i.e., FIG. 2B). The dual inspiration valves that are connected to the blower box allow a sufficient amount of pressurized air to enter the mask quickly, providing therapeutic pressure to the patient almost instantaneously after the onset of an apnea event. Further, the inspiratory membrane 140 for both inspiratory valves is perpendicular to the channel formed by the valve housing 120, such that the pressurized air can enter the mask in sufficient volume with a slight bend in the direction of flow, as shown in FIG. 8. This promotes more laminar and less restricted flow, which allows for near-instantaneous pressurization of the mask.

Figure 9A:
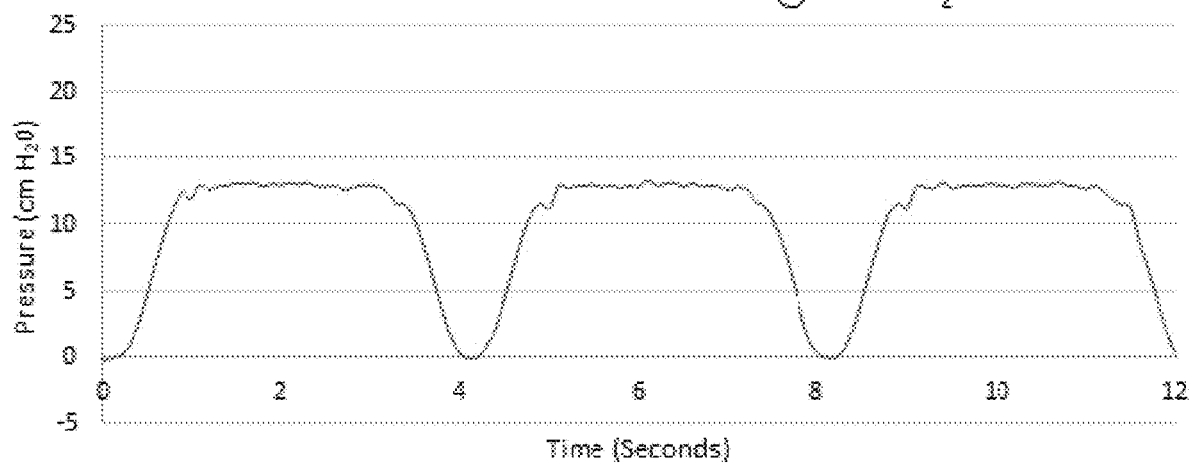
FIG. 9A illustrates the therapeutic pressure delivery of the novel valve structure for a tidal volume of 350 cc.
Figure 9B:
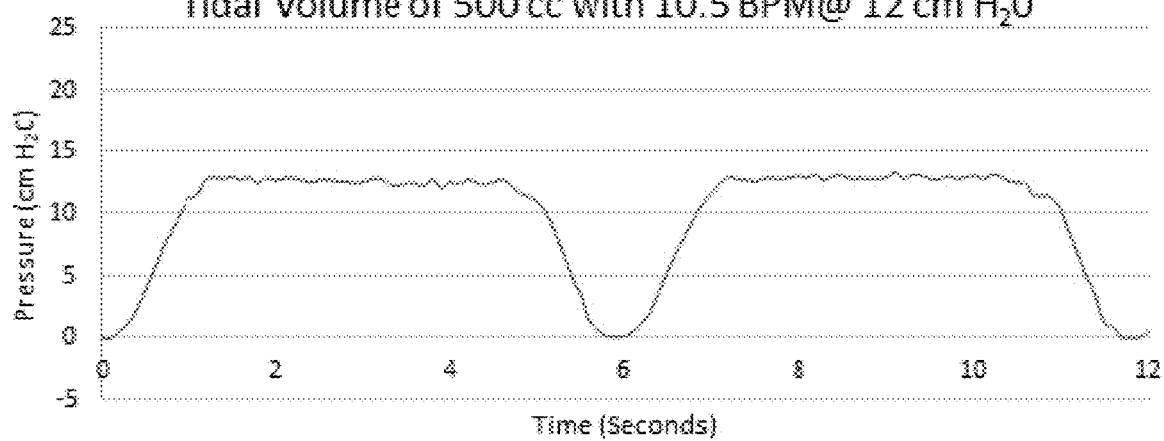
FIG. 9B illustrates the therapeutic pressure delivery of the novel valve structure for a tidal volume of 500 cc.

The design of the valve structure is also robust in that it can be used with all patients, regardless of breathing rate or per breath volume. For example, as shown in FIG. 9A, the valve is subjected to 15 breaths/minute with a tidal volume of 350 cc. The valve structure can maintain the set therapeutic pressure of 12 cm of H$_2$O throughout the breathing cycle. And as already discussed, should the patient experience an apnea event, the therapeutic pressure would be delivered to the mask nearly instantaneously providing the therapeutic pneumatic splint that maintains the patient's airway open reversing the apnea event. The same mask can provide therapeutic pressure for a different patient with, for example, 10.5 breaths/minute with a tidal volume of 500 cc as shown in FIG. 9B. In spite of a nearly 50% increase in tidal volume, the valve structure still maintains therapeutic pressure. While these are just two examples, the valve structure can accommodate tidal volumes ranging from 0 to 800 cc, with breath/minute ranging from 0 to 18. These ranges will accommodate nearly every patient suffering from sleep apnea. Moreover, while the therapeutic pressure shown in FIGS. 7A-7D and 9A-9B is 12 cm of H$_2$O, the pressure is fully adjustable and may be increased or decreased. The performance of the valve structure, including the near-instantaneous pressurization is not affected by the set therapeutic pressure.

Now a novel standoff feature will be described. It would be desirable to reduce the sensation of the expiratory valve opening. Additionally, it would be useful to reduce pressure during expiration to provide a comfort benefit to the user. By adding a standoff feature in the valve to prevent the membrane from fully forming convex during exhalation. The standoff would allow the distensible membrane to fully form a concave state against the vent valve seat, but would not allow the membrane to fully flex convex during exhalation. Further the standoff would form a secondary valve seat. FIGS. 10A-10F illustrate the valve structure with the standoff. The dashed arrows in these figures denote air flow movement.

Figure 10B:
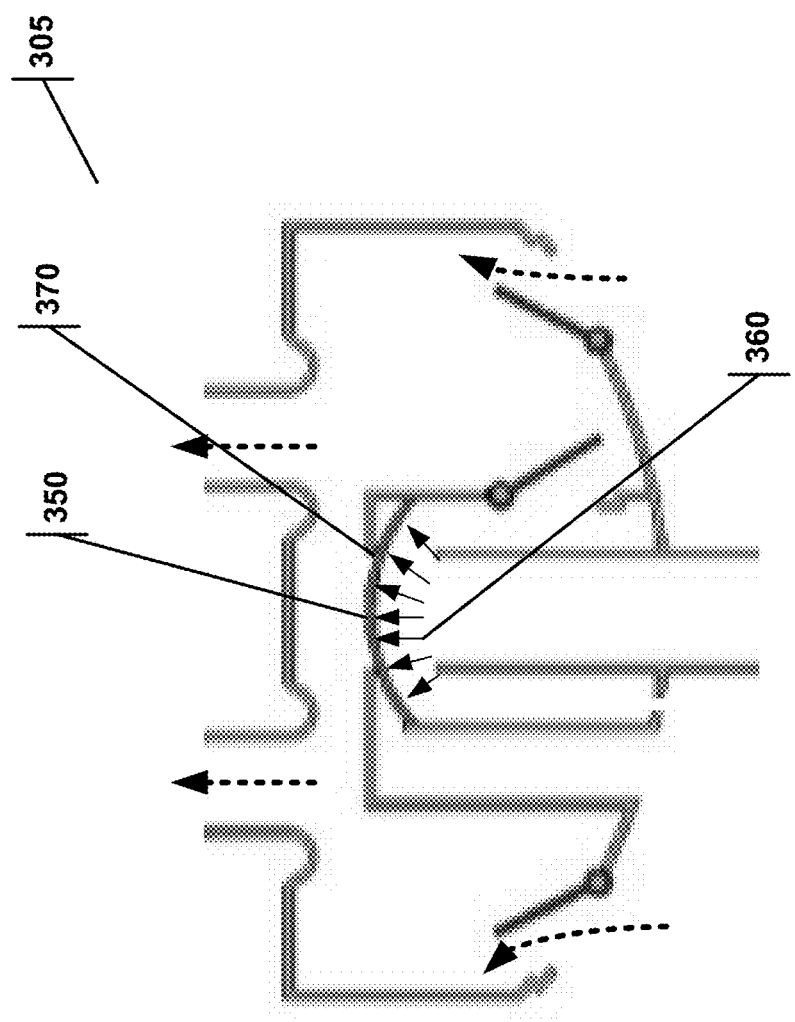
FIG. 10B illustrates a novel valve structure with a standoff, during inhalation with pressurized airflow.

Referring to FIG. 10A, the valve structure 305 has a standoff 310 that forms a secondary valve seat 320. The valve structure 305 has similar inspiratory valves 330, as well as the pressurized inlet valve 340 in the previously described embodiments. Those valves operate similar to the embodiments already described in the inspiratory, expiratory and rest/apnea modes. The standoff 310, however, affects the operation of the expiratory valve and makes it easier for the patient to open the expiratory valve—increasing patient comfort and reducing noise. FIG. 10B illustrates the valve structure 305 when the blower is on and providing pressurize air. This is the inhalation phase, and the pressurized air from the blower acts on the entire underside of the expiratory membrane 350, as shown by pressure arrows 360. Also, the membrane 350 forms the seal using the primary valve seat 370.

Figure 10C:
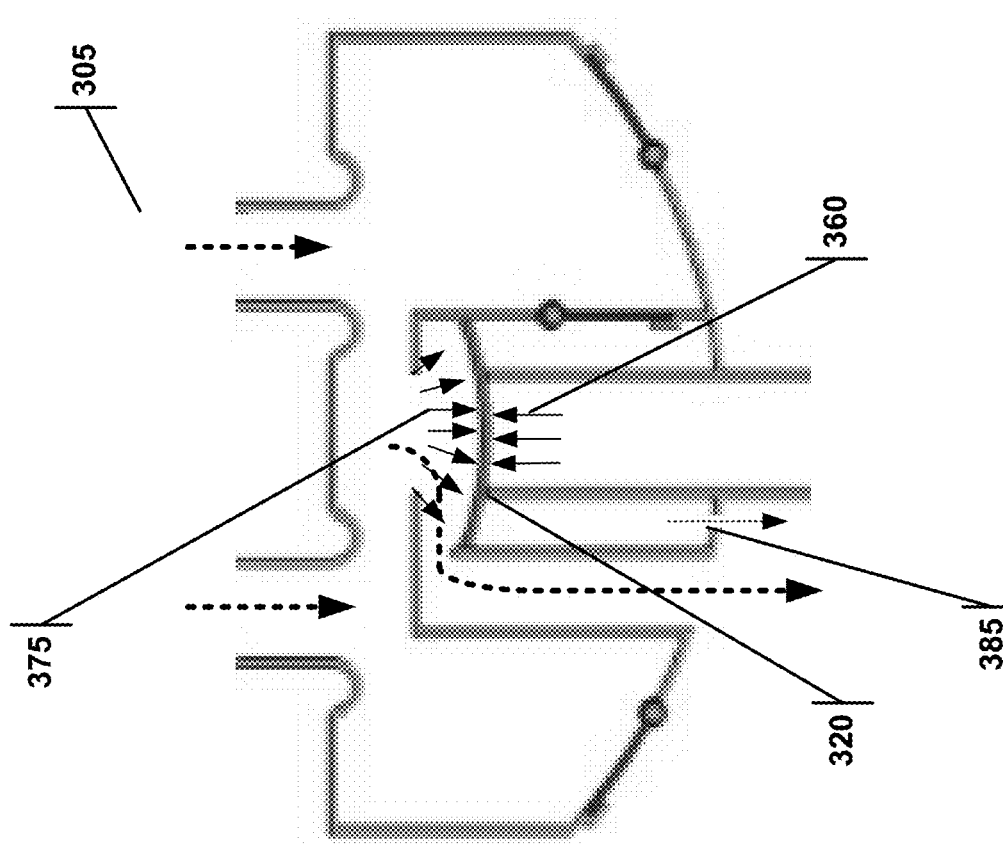
FIG. 10C illustrates a novel valve structure with a standoff, during expiration with pressurized airflow.

FIG. 10C is the expiratory phase, when the blower is providing pressurized air. The patient provides the pressure needed to open the expiratory valve, as shown by pressure arrows 375, but the valve now seals on the secondary valve seat 320. On the opposite side of the expiatory membrane is the pressure exert by the blower air, shown by pressure arrows 360. What is important to note is that the pressure exerted by the patient is over a much larger area of the expiratory membrane than the area over which the pressure from the blower exerts. This means that once the expiratory valve is sealed it takes less pressure than the blower box is providing to keep the expiratory valve sealed. To further assist the complete seal during the expiratory phase, the valve structure 305 may have a small opening 385 that allows a small intended leak so that the volume on the opposing side of the expiratory membrane from the patient can be depressurized.

Having a dual seat structure for the expiratory valve increases the patient comfort. Specifically, when a patient begins the expiratory phase of breathing, it is generally with a pressure and volume that is initially high and then tapers off some during expiration. Without a dual seat design, a patient might initially have sufficient expiration to open the expiratory valve, but as the expiratory phase continues the expiration tapers potentially to a point where there is an insufficient force to keep the expiratory valve opened. Not having a dual seat design would have therefore cut off the natural expiratory phase of the breathing cycle and cause discomfort for the patient.

With the dual seat design, the initial force of the expiration opens the expiratory valve and seals the valve on the secondary seat formed by the standoff. As the expiration tapers off, there remains sufficient pressure to keep the valve sealed against the secondary seat until the patient naturally pauses in breath to being the inhalation phase. This is much more comfortable for the patient.

Figure 10D:
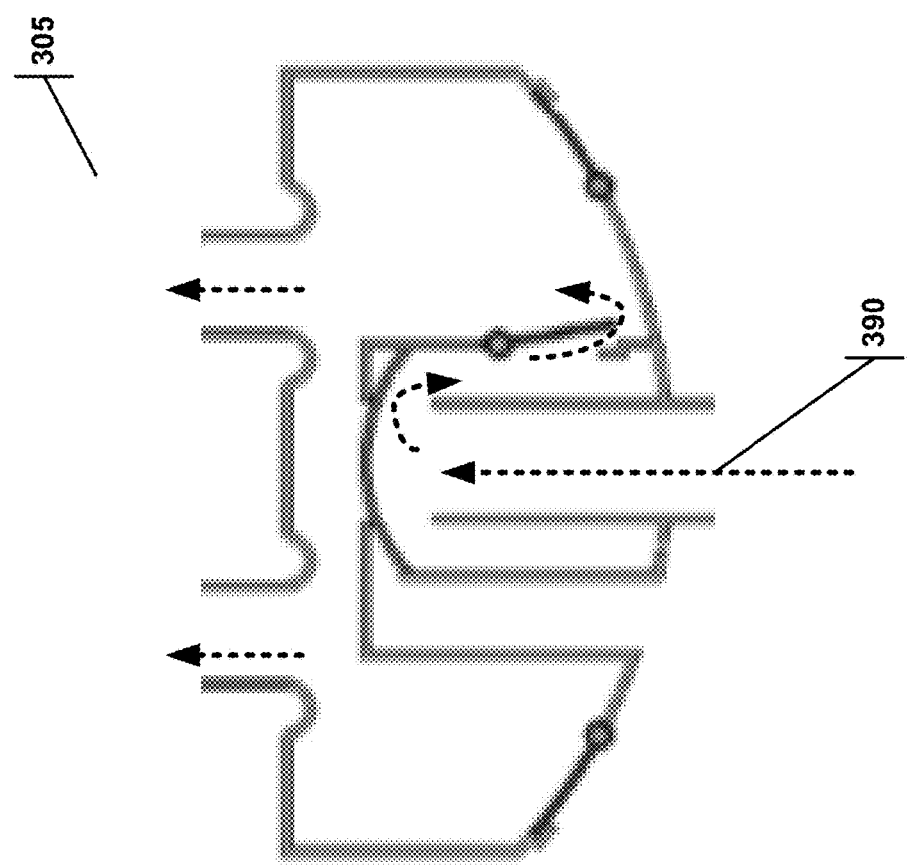
FIG. 10D illustrates a novel valve structure with a standoff, during an apnea event with pressurized airflow.

FIG. 10D illustrates the valve structure 305 during an apnea event. Its operation is similar to those discussed above in conjunction with arrow 390 showing the path of the pressured air.

Figure 10E:
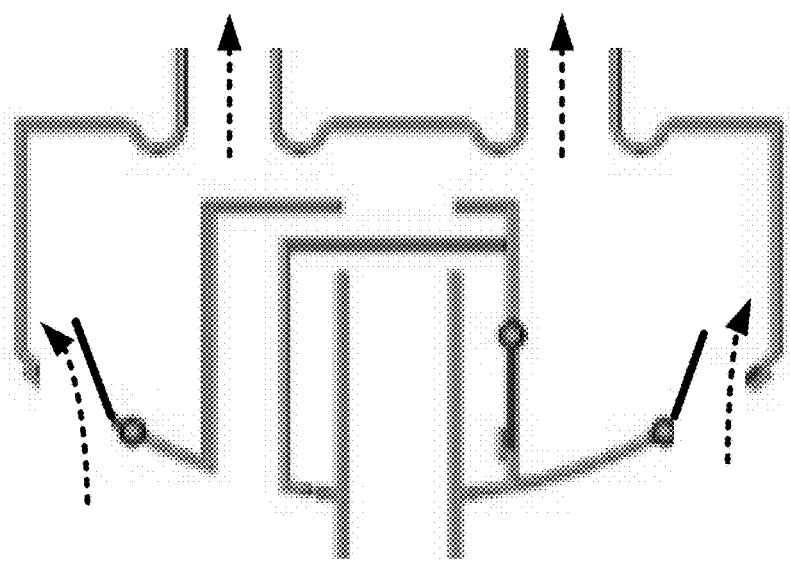
FIG. 10E illustrates the valve states for a novel valve structure with a standoff for the inspiration mode when the blower box is disconnected.
Figure 10F:
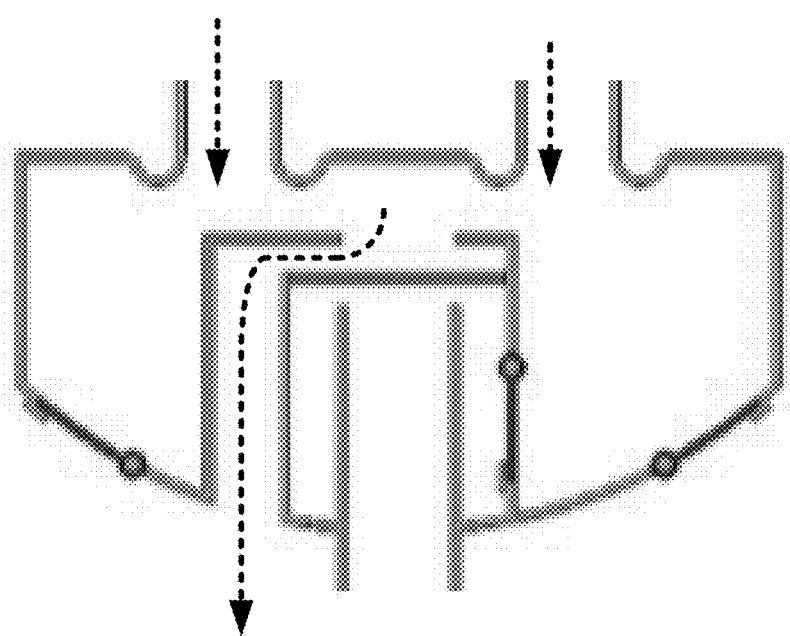
FIG. 10F illustrates the valve states for a novel valve structure with a standoff for the expiration mode when the blower box is disconnected.

Finally FIGS. 10E and 10F illustrate the valve states for the inspiration and expiration when the blower box is disconnected.

As with the embodiments discussed above, the design of valve structure 305 allows for near instantaneous pressurization during an apnea event, regardless when in the respiration cycle the event occurs. The same valve structure is robust enough to be used across a wide range of tidal volumes and breaths/minute.

Since the present the nasal pillow/mask 15 does not require the blower to run continuously, in various example embodiments a PAP blower may be initiated in response to a preset delay, or in response to a detected onset of sleep or attainment of a preselected sleep stage, to enable a user to fall asleep while the blower is off. Accordingly, various example aspects of an airflow generator with delayed onset will now be described with reference to FIGS. 11-13.

Currently, human sleep stages are typically determined using a laboratory-based measurement called polysomnography. In polysomnography, it is typical for several electro-encephalogram readings to be taken (EEGs are the microvolt potentials generated by brain activity that can be measured at the scalp using electrodes), in addition to other parameters such as respiration, electrocardiogram (ECG), leg movements, and electro-oculograms (EGG). Based on work originally pioneered by Rechtschaffen and Kales (R&K), it is now conventional to score human sleep in 30-second epochs, and to label these epochs using sleep stage labels.

At present, the American Academy of Sleep Medicine defines the stages of sleep as:

Wake—this is when a person is fully awake, and is characterized by a positive dominant rhythm in the occipital EEG channel (when eyes are closed), typically in the range of 8 to 14 Hz (often referred to as alpha waves).

Stage N1—this is the lightest stage of sleep, and is characterized by the appearance of some low amplitude waves at multiple frequencies interspersed with the alpha waves for more than 50% of an epoch. There may also be sharp vertex waves, some slow eye movements on the EGG and/or an overall lowering of the frequency of EEG.

Stage N2—this is a slightly deeper stage of sleep, and is marked by the appearance of sleep spindles and K-complexes, on a background of mixed frequency signals. Sleep spindles are bursts of higher frequency activity (e.g., greater than 12 Hz). K-complexes are distinct isolated bipolar waves lasting about 1-2 seconds.

Stage N3 is the deepest stage of sleep (in the original R&K classification, there were two distinct stages called Stage 3 and Stage 4). This is characterized by the appearance of slow waves (e.g., 1-2 Hz frequency) for at least 20% of an epoch.

Stage R (REM)—this is rapid eye movement sleep, and is apparent through the presence of distinct activity in the EOG signal. The EEG signals recorded are typically quite similar to Stage N1 or even wake.

An automated system for scoring polysomnogram data is described in U.S. Pat. No. 5,732,696 to Rapoport et al., which is incorporated herein by reference. The system uses a computer to look for elemental patterns in the PSG data (such as the sleep spindles described above), and then uses a probabilistic weighting to score each epoch. However, this approach to the problem of determining sleep stages is limited by the technical difficulty of measurement of a full set of polysomnogram signals, and hence is difficult and cumbersome to implement for more than a single night.

A number of systems have provided alternative techniques for determining sleep stage. One approach is to use actigraphy, in which small motion sensors (e.g., accelerometers) are worn by a user, typically in a wristwatch configuration in some cases referred to as activity trackers. Such systems may be able to effectively distinguish between sleep and wake, but may not effectively distinguish between different sleep states.

US2006/0184056 (Heneghan et al.), which is incorporated herein by reference, describes a sleep monitoring system which uses an ECG signal which is processed to determine a status for each epoch, either apneic or normal.

WO2007143535 (Heneghan et al.), which is incorporated herein by reference, describes a system for monitoring physiological signs such as sleep state by monitoring motion, breathing, and heart rate signals obtained in a non-contact fashion. A classifier model is applied to the streams of data.

A system which combines ECG and respiration methods to determine a simplified sleep stage is described in US20090131803 (Heneghan et al.), which is incorporated herein by reference. This combines signal characteristics derived from cardiogram and respiration signals, such as the amplitude modulation of the ECG signal and the dominant respiratory frequency in order to distinguish sleep from wakefulness.

WO2004112606 (Heneghan et al.), which is incorporated herein by reference, describes a method of detecting sleep apnea using trans-cervical bioimpedance measurements.

US2011/0124979 (Heneghan et al.), which is incorporated herein by reference, describes an approach to sleep monitoring using ECG and photoplethysmogram (PPG) data. These may be sensed using a Holter monitor and a pulse oximeter which are wearable in an ambulatory manner.

An approach in which cardiac R-R wave intervals are used to designate sleep as REM or non-REM is described in U.S. Pat. No. 5,280,791 to Lavie, which is incorporated herein by reference. A power spectrum of the cardiac R-R interval is calculated in order to determine the stages of sleep.

US2014/0088373 (Phillips et al.), which is incorporated herein by reference, discloses a system that is said to be able to differentiate between sleep states. A processor determines a sleep stage based on a combination of bodily movement and respiration variability. The determination of sleep stages may distinguish between deep sleep and other stages of sleep, or may differentiate between deep sleep, light sleep and REM sleep. The bodily movement and respiration movement signals may be derived from one or more sensors, such as a non-invasive sensor (e.g., a non-contact radio-frequency motion sensor or a pressure sensitive mattress).

Any of a variety of commercially available wearable or portable activity trackers are also equipped with sleep detection capabilities, such as: FIT BIT (Fitbit Inc. 405 Howard Street, San Francisco, Calif. 94105); SENSE and SLEEP PILL (Hello Inc, 1660 17th Street, San Francisco, Calif. 94107); Beddit (Misfit); MisfitShine (Misfit); and Withings Aura™, for example.

Conventional breathing devices such as CPAP systems must have the blower operating while the user is wearing the mask. The blower is typically set to a minimum of 4 cm $H_2O$. This is necessary because without the blower delivering fresh air, the user re-breaths residual exhalations that migrate into and out of the hose. The blower is not continuously flushing out the stale air from the hose when turned off in conventional CPAP. The blower creates noise and perceptible air flow, interfering with the wearer's ability to go to sleep.

The system of the present invention eliminates the need for the blower to operate while the user is attempting to go to sleep. It may also have a much smaller caliber hose, such as 50% smaller in diameter. This has a significant volume reduction, hence significantly less potential for "re-breath air" to reside. Also, a preferred embodiment has a one-way flapper valve on the air supply path which prevents exhaled breath from migrating into the hose. While prior art systems need to maintain around a minimum flow rate corresponding to 4 $cmH_2O$ of pressure while the user tries to go to sleep over the noise, the blower in the system of the present invention can be shut off while the user is trying to go to sleep. The blower is instead not turned on until a delayed start time T. Time T can be preselected as a delay from initiation of the clock and measured in time such as in minutes or hours. Alternatively, T can be a set time of day programmed in by the user or care giver, based upon their experience how long it takes that user to go to sleep, or a time at which the onset of sleep is detected using any of a variety of sleep detectors.

Figure 11:
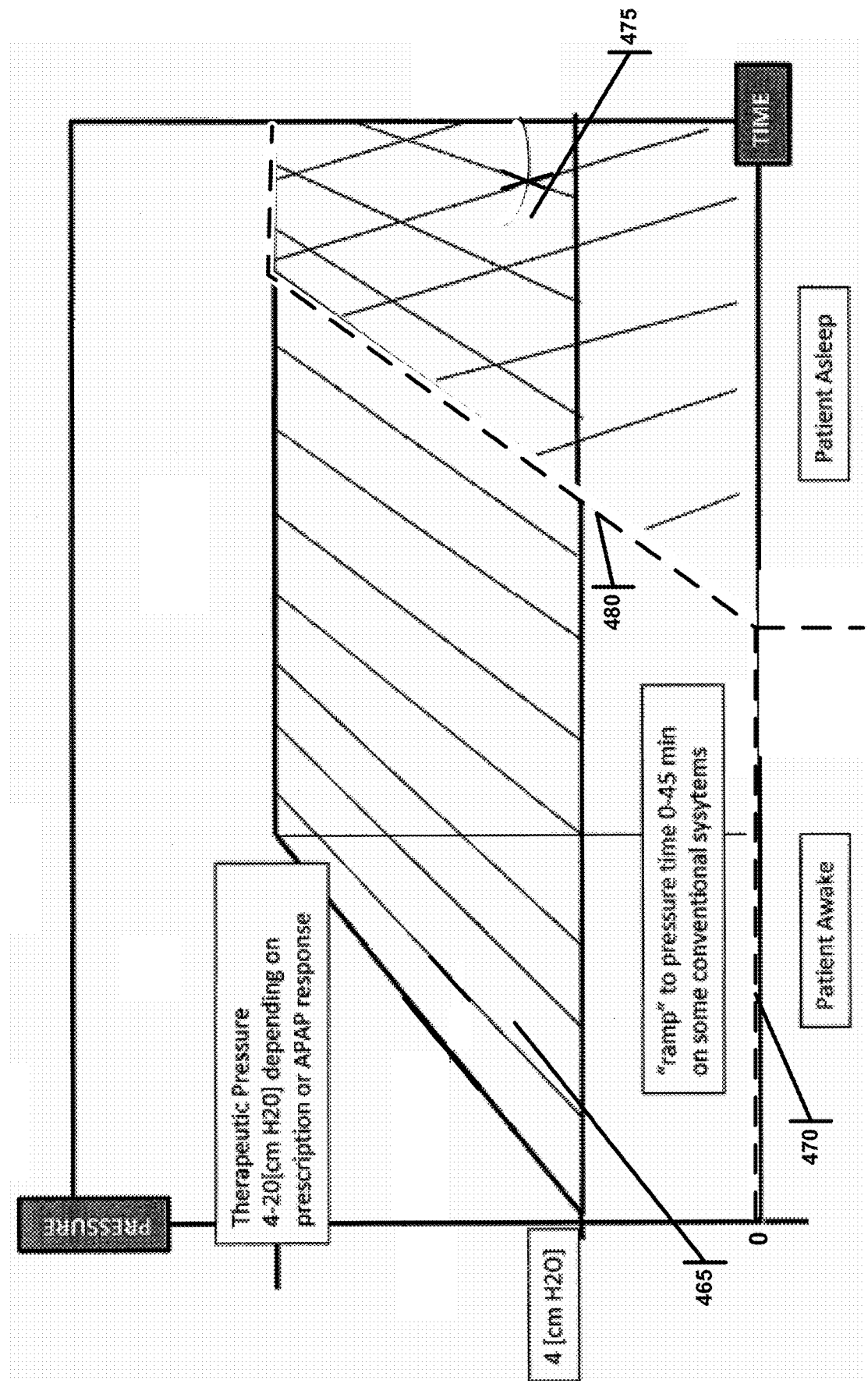
FIG. 11 is a chart showing example pressures applied by an example PAP system at various times, according to various example embodiments.

Graphically, conventional systems must operate in the hashed area 465 shown in FIG. 11, with an air flow of at least about 4 $cmH_2O$ at all times that the mask is worn by the user, and ramping to higher flow rates.

The present system operates on the datum line 470 and in the hashed area 475 shown above the datum line 470. The air flow rate from the blower can be zero while the user is awake, and the blower can remain off until after the user has fallen asleep. After the onset of a sleep state, the blower can turn on and subsequently ramp up 480 to the desired therapeutic flow rate. This is advantageous because it eliminates the sensation of forced airflow, and eliminates noise from the blower box, while the user is trying to go to sleep. Also, this preserves the ability to speak naturally prior to sleep.

The present system can work with the blower off indefinitely. In one embodiment the blower is off at the start of use and turns on at a preset time delay following activation of the timing cycle. The time delay can either be programmed into the machine or selectable by the physician or user (an off time could also be set for an anticipated wake-up). The user may select or input a delay such as at least about 5 minutes, or at least about 10, 15, or 30 minutes, or up to an hour or more, for example. The blower will automatically turn on at delayed start time T and begin to ramp up in air flow when the preset delay period has expired. Alternatively, the user can select a start time of day such as 10:00 PM or 11:00 PM by which time the user expects to be asleep.

Alternatively, the blower can turn on in response to a determination that the user has fallen asleep or reached a particular sleep stage. Sleep sensors may be employed to determine when the user achieves a sleep state. In response to the detection of the onset of sleep, the blower is turned on and ramps to the desired therapeutic flow rate. The sleep sensors may be carried by the system, or may be a remote device that is in wireless or wired communication with the system. Any of the sleep detection devices discussed elsewhere herein can be utilized to determine the onset of sleep.

Thus, one or more biometric monitoring devices may automatically detect or determine when the user is attempting to go to sleep, is entering sleep, is asleep, and/or is awoken from a period of sleep. In such embodiments, the biometric monitoring device may employ physiological sensors to acquire data and the data processing circuitry of the biometric monitoring device may correlate a combination of heart rate, heart rate variability, respiration rate, galvanic skin response, motion, skin temperature, and/or body temperature data collected from sensors of the biometric monitoring device to detect or determine if the user is attempting to go to sleep, is entering sleep, is asleep, and/or is awoken from a period of sleep. For example, a decrease or cessation of user motion combined with a reduction in user heart rate and/or a change in heart rate variability may indicate that the user has fallen asleep. Subsequent changes in heart rate variability and galvanic skin response may then be used by the biometric monitoring device to determine transitions of the user's sleep state between two or more stages of sleep (for example, into lighter and/or deeper stages of sleep). Motion by the user and/or an elevated heart rate and/or a change in heart rate variability may be used by the biometric monitoring device to determine that the user has awoken. Additional details can be found in US patent publication 20140278229 to Hong, et al., assigned to Fitbit, Inc., the disclosure of which is hereby incorporated in its entirety herein by reference.

The PAP system of the present invention thus includes an input for receiving a signal indicative of the onset of sleep or a change in a stage of sleep. The input may be a wired port or a wireless port. Preferably but not necessarily, a wireless port is provided in the form of a transceiver for wireless pairing with any of a variety of commercial devices capable of determining sleep state.

These include any of a variety of commercial activity trackers (e.g., Fitbit, Jawbone, Under Armour, UP, Resmed S+) or with a sleep detection bed (e.g., Sleep Number) or with any of a variety of dedicated sleep detection systems that can be either integrated into the device or separate but connectable via wireless or hard-wired connection.

In another embodiment sleep/apnea sensors are employed to turn the machine on only when both sleep and apnea are occurring. In either case, the sleep sensors could also do the opposite function and turn the blower off when waking is sensed. Suitable sleep apnea detection systems are disclosed in U.S. Patent Publication No. 2014/0200474, the disclosure of which is incorporated by reference in its entirety herein.

The advantages of being able to wear a PAP mask with no blower operating include: comfort from force airflow while awake; talking without the difficulty of forced air; less noise while attempting to sleep; and reduction of wasted power, particularly battery power.

Figure 12:
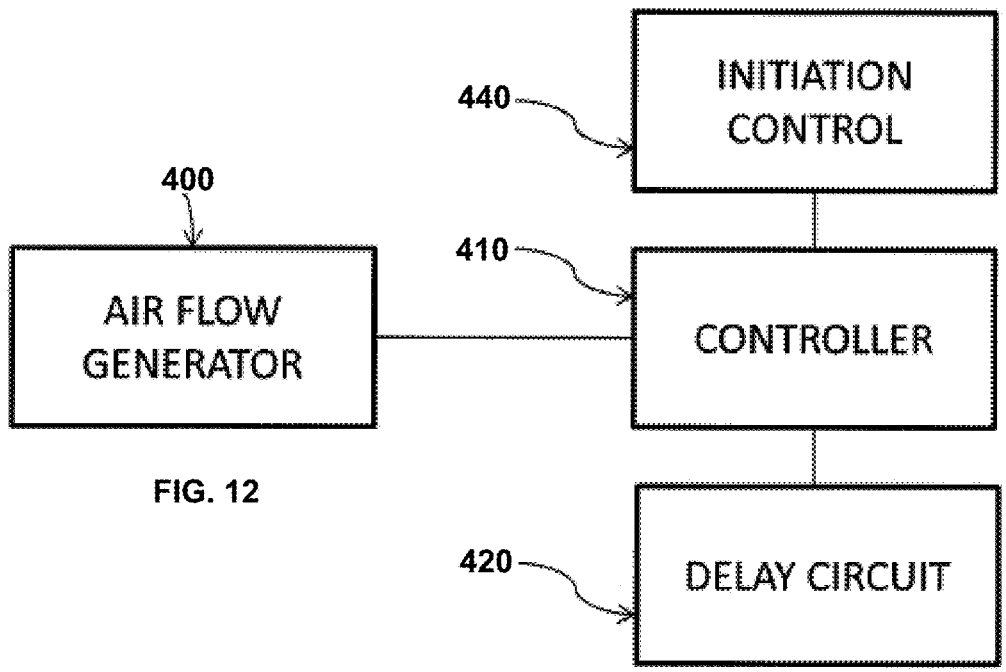
FIG. 12 is a diagram depicting example relationships among example components of an example PAP system operated in part by a delay circuit, according to various example embodiments.

Referring to FIG. 12, the present system may comprise a mask/hose and a blower box with an air flow generator 400, a controller 410 and a delay circuit 420. An initiation control 440 is provided for the user to initiate a delay cycle. The initiation control can be a button, switch, touch screen or other control.

Figure 13:
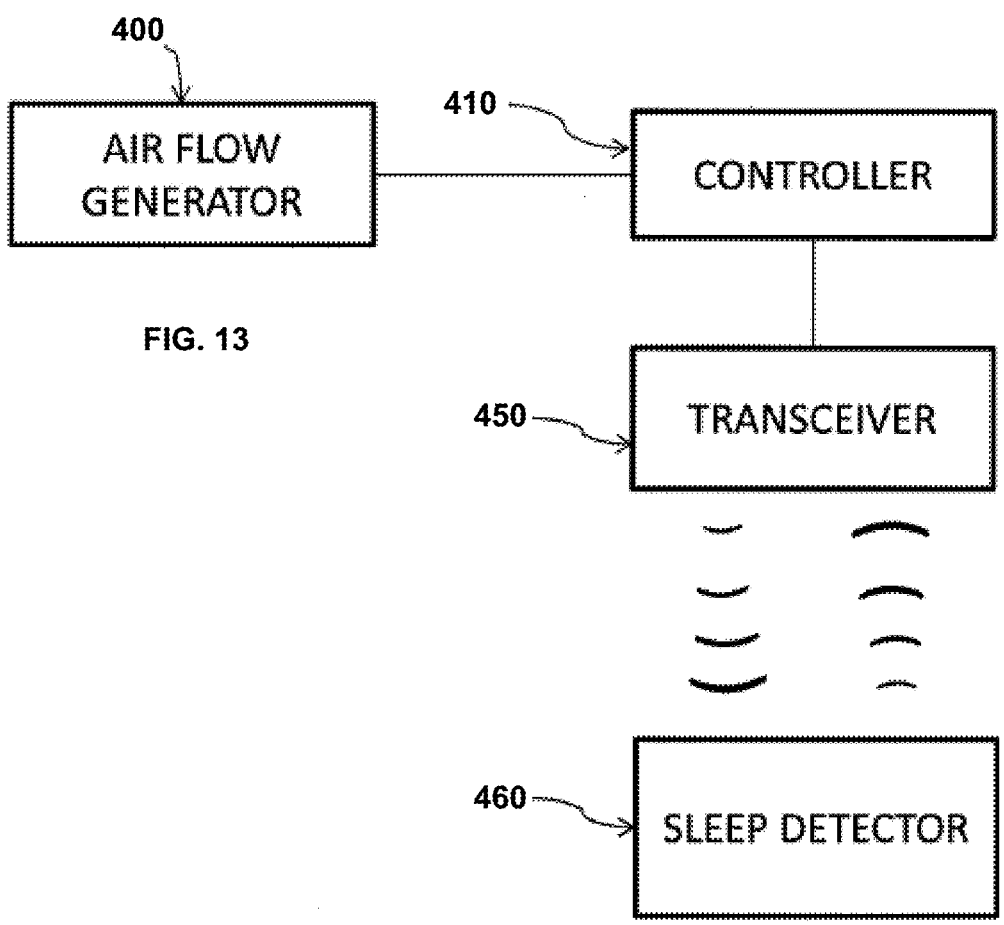
FIG. 13 is a diagram depicting example relationships among example components of an example PAP system operated in part by a sleep detector, according to various example embodiments.

The present system has the ability to communicate with accessory devices. This communication can come from mechanical or pneumatic feedback, but preferably but not necessarily is electronic communication transmitted over a wire or wireless. Most preferably but not necessarily, the present system has "Bluetooth" or other wireless communication with accessory sleep detection devices. The communication features could be in any component, but most preferably but not necessarily is in the blower box. Referring to FIG. 13, the controller 410 is in electrical communication with a transceiver 450 which may be permanently or removably carried by the housing as discussed herein. The transceiver 450 can be paired into wireless communication with a sleep detector 460.

The wireless communication module 450 and associated antenna carried by the PAP device thus provide a wireless connection between the CPAP device and a paired sleep detection device 260 such as any of those discussed herein. Preferably but not necessarily, the sleep detector is a wearable device such as an activity tracker. Pairing may be accomplished utilizing any of a variety of short-range wireless protocols appropriate for the particular sleep detection device, such as Wi-Fi, Zigbee, Bluetooth, wireless HDMI and/or IEEE 802.11 protocols (e.g., 802.11 G, 802.11N, 802.11AC, or the like). Other examples of potential communication protocols include iBeacon, Z-Wave, WirelessHART/Dust Networks, ISA 100a, ISM-band-based channels, IMBI, ANT or ANT+, or other methods of communication.

For the purposes of the present disclosure, the term "ANT" is intended to include "ANT+and refers to a proprietary wireless sensor network technology featuring a wireless communications protocol stack that enables semiconductor radios operating in the 2.4 GHz industrial, scientific, and medical allocation of the RF spectrum ("ISM band") to communicate by establishing standard rules for co-existence, data representation, signaling, authentication, and error detection. ANT is characterized by a low computational overhead and low to medium efficiency, resulting in low power consumption by the radios supporting the protocol.

For the purposes of the present disclosure, the term "Bluetooth®" refers to a wireless technology standard for exchanging data over short distances (using short-wavelength radio transmissions in the ISM band from 24000-2480 MHz) from fixed and mobile devices, creating personal area networks (PANs) with high levels of security. Created by telecom vendor Ericsson in 1994, it was originally conceived as a wireless alternative to RS-232 data cables. It can connect several devices, overcoming problems of synchronization. Bluetooth® is managed by the Bluetooth® Special Interest Group, which has more than 18,000 member companies in the areas of telecommunication, computing, networking, and consumer electronics. Bluetooth® was standardized as IEEE 802.15.1, but the standard is no longer maintained.

A wireless LAN may exist using a different IEEE protocol, 802.11 b, 802.11 g or possibly 802.11n. The defining characteristics of LANs, in contrast to WANs (wide area networks), include their higher data transfer rates, smaller geographic range, and lack of a need for leased telecommunication lines. Current Ethernet or other IEEE 802.3 LAN technologies operate at speeds up to 10 Gbit/s.

For the purposes of the present disclosure, the term "low powered wireless network" refers to an ultra-low powered wireless network between sensor nodes and a centralized device. The ultra-low power is needed by devices that need to operate for extended periods of time from small batteries energy scavenging technology. Examples of low powered wireless networks are ANT, ANT+, Bluetooth Low Energy (BLE), ZigBee and WiFi.

For the purposes of the present disclosure, the term "ZigBee" refers to a specification for a suite of high-level communication protocols used to create personal area networks built from small, low-power digital radios. ZigBee is based on an IEEE 802 standard. Though low-powered, ZigBee devices often transmit data over longer distances by passing data through intermediate devices to reach more distant ones, creating a mesh network; i.e., a network with no centralized control or high-power transmitter/receiver able to reach all of the networked devices. The decentralized nature of such wireless ad-hoc networks makes them suitable for applications where a central node can't be relied upon. ZigBee may be used in applications that require a low data rate, long battery life, and secure networking. ZigBee has a defined rate of 250 Kbit/s, best suited for periodic or intermittent data or a single signal transmission from a sensor or input device. The technology defined by the ZigBee specification is intended to be simpler and less expensive than other WPANs, such as Bluetooth® or Wi-Fi. Zigbee networks are secured by 128-bit encryption keys.

Suitable wireless pairing protocols between the PAP device and remote activity tracker or other sleep detection device are disclosed in US patent publication 2014/0281547, entitled Wireless Pairing of Personal Health Device with a Computing Device, the disclosure of which is hereby incorporated by reference in its entirety herein.

Since different currently available activity trackers may utilize different protocols (e.g., some may utilize Bluetooth, others may utilize ANT or ANT+), the communication module 250 carried by the PAP device of the present invention is preferably but not necessarily able to pair utilizing any of a variety of protocols so that it can universally obtain sleep onset data from whatever device the user may choose to utilize. Thus, the communication module may be provided with a capability to communicate utilizing at least two and preferably but not necessarily at least three or four or more different protocols. It can be programmed to detect the appropriate protocol from a sleep detector in range and select that protocol automatically for a given activity tracker or another source device. Alternatively, a user may be provided with a choice from an array of different communication modules from which they can select the module capable of communication with their sleep onset detector. The selected module can then be plugged into a transceiver docking port on the CPAP device followed by pairing as is understood in the art. The CPAP device may thus be provided with a port for removably receiving the selected communication module.

The accessory devices that the present system communicates with can be various items that have the ability to sense sleep onset and or sleep stage. Exemplary accessory devices can sense sleep state in a variety of ways: movement, breath rate, blood pressure, heart rate, eye motion, temperature, sound, brain activity, physiological activity such as kidney function, GI function, hormone production and delivery. Such accessory devices may comprise a Fitbit or another accessory device that already has sleep sensing capabilities, and may communicate, for instance wirelessly, with the blower box and tell it whether the person is asleep or awake, so that the blower box can respond by turning on or off based on the sleep state that is reported to it.

From observing changes in behavior and responsiveness, scientists have noted the following characteristics that accompany and in many ways define sleep: sleep is a period of reduced activity; sleep is associated with a typical posture, such as lying down with eyes closed in humans; sleep results in a decreased responsiveness to external stimuli; sleep is a state that is relatively easy to reverse (this distinguishes sleep from other states of reduced consciousness, such as hibernation and coma).

From observations of behavioral changes that accompany sleep and simultaneous physiological changes, scientists now define sleep in humans based on brain wave activity patterns and other physiological changes as described below.

Many physiological variables are controlled during wakefulness at levels that are optimal for the body's functioning. A person's temperature, blood pressure, and levels of oxygen, carbon dioxide, and glucose in the blood remain quite constant during wakefulness. During sleep, however, physiological demands are reduced and temperature and blood pressure drop. In general, many physiological functions such as brain wave activity, breathing, and heart rate are quite variable when a person is awake or during REM sleep, but are extremely regular when a person is in non-REM sleep.

For centuries, physicians believed that sleep was a period of brain inactivity, yet research over the last 60 years has shown us that the brain remains active during sleep. There is a progressive decrease in the activation or "firing" rate of most neurons throughout the brain as sleep progresses from wakefulness to non-REM sleep. Also, the patterns of neuron firing change from a seemingly random and variable activity pattern during wakefulness, to a much more coordinated and synchronous pattern during non-REM sleep.

During REM sleep (the stage of sleep most associated with dreaming) there is an increase in the firing rate of most neurons throughout the brain, as compared to non-REM sleep. In fact, the brain in REM sleep can even be more active than when awake. Patterns of brain activity during REM sleep are more random and variable, similar to during wakefulness. This pattern of brain activity during REM sleep probably underlies the intense dreaming that occurs during this state.

Through a process known as thermoregulation, the temperature of our body is controlled by mechanisms such as shivering, sweating, and changing blood flow to the skin, so that body temperature fluctuates minimally around a set level during wakefulness. Just before a person falls asleep, their body begins to lose some heat to the environment, which some researchers believe actually helps to induce sleep. During sleep, the body's central set temperature is reduced by 1 to 2° F. As a result, people use less energy maintaining their body temperature. It has been hypothesized that one of the primary functions of sleep is to conserve energy in this way.

Body temperature is still maintained, although at a slightly reduced level during non-REM sleep, but during REM sleep body temperature falls to its lowest point. Sleeping under a blanket during the usual 10-to 30-minute periods of REM sleep ensures that people do not lose too much heat to the environment during this potentially dangerous time without thermoregulation.

Breathing patterns also change during sleep. When a person is awake, breathing is usually quite irregular, since it is affected by speech, emotions, exercise, posture, and other factors. As a person progresses from wakefulness through the stages of non-REM sleep, their breathing rate slightly decreases and becomes very regular. During REM sleep, the pattern becomes much more variable again, with an overall increase in breathing rate.

One of the possible functions of sleep is to give the heart a chance to rest from the constant demands of waking life. As compared to wakefulness, during non-REM sleep there is an overall reduction in heart rate and blood pressure. During REM sleep, however, there is a more pronounced variation in cardiovascular activity, with overall increases in blood pressure, heart rate, and blood flow.

For the most part, many physiological activities are reduced during sleep. For example, kidney function slows and the production of urine is decreased. However, some physiological processes may be maintained or even increased during sleep. For example, one of the greatest changes induced by sleep is an increase in the release of growth hormone. Certain physiological activities associated with digestion, cell repair, and growth are often greatest during sleep, suggesting that cell repair and growth may be an important function of sleep.

One of the most notable but least understood characteristics of sleep is dreaming, during which a person's thoughts may follow bizarre and seemingly illogical sequences, sometimes random and sometimes related to experiences gathered during wakefulness. Visually intense dreaming occurs primarily during REM sleep. However, not all dreams occur during REM sleep. For example, night terrors actually occur during non-REM sleep.

Varying explanations for dreaming, as well as the meanings of dreams, have been offered by philosophers and psychologists throughout history. Even with recent scientific investigations of dreaming, dreams still remain something of a mystery. Some experts suggest that dreams represent the replay of the day's events as a critical mechanism in the formation of memories, while others claim that the content of dreams is simply the result of random activity in the brain.

Any of the suitable technologies and materials set forth and incorporated herein may be used to implement various example aspects of the invention as would be apparent to one of skill in the art.

While CPAP is used throughout this disclosure, it would be apparent to those of skill in the art that the devices, methods and structures disclosed in this application may be used in systems that do not require or use constant positive airway pressure. Indeed, as shown in FIG. 11 herein and in the related discussion, the pressure need not be constant. Thus, the teachings herein are not limited to CPAP but apply equally to PAP (Positive Airway Pressure) systems and treatments for sleep apnea.

Although exemplary embodiments and applications of the invention have been described herein including as described above and shown in the included example Figures, there is no intention that the invention be limited to these exemplary embodiments and applications or to the manner in which the exemplary embodiments and applications operate or are described herein. Indeed, many variations and modifications to the exemplary embodiments are possible as would be apparent to a person of ordinary skill in the art. The invention may include any device, structure, method, or functionality, as long as the resulting device, system or method falls within the scope of one of the claims that are allowed by the patent office based on this or any related patent application.

The invention claimed is:

1.

A valve structure for treating a patient suffering form obstructive sleep apnea, the valve structure adapted to be connected to an air flow generator and connected to a mask that covers at least the nostrils of a patient, the valve structure comprising:

an inlet pressure port constructed to be attached to the airflow generator;

an expiration valve comprising an expiratory membrane constructed to prevent air flow across the expiratory membrane, and a primary seat and a secondary seat, wherein during inspiration by the patient the expiratory membrane forms a seal with the primary seat directing a first airflow around the expiratory membrane, and wherein during expiration by the patient the expiratory membrane forms a seal with the secondary seat directing a second airflow around the expiratory membrane;

an opening constructed to evacuate a portion of air flow from the air flow generator over the secondary seat to an outside of the mask, during expiration; and an inspiration valve constructed to allow a third air flow from the outside of the mask into the mask with substantially no resistance and block air flow from within the mask to the outside of the mask.

2.

The valve structure of claim 1, the expiration valve further comprises an opening pressure, and the opening pressure is variable and dependent on a pressure of air in the inlet pressure port as follows: (1) the opening pressure of the expiration valve increases when the pressure of air in the inlet pressure port increases; and/or (2) the opening pressure of the expiration valve decreases when the pressure of air in the inlet pressure port decreases.

3.

The valve structure of claim 1, wherein the inspiration valve comprises two valves.

4.

The valve structure of claim 1, further comprises an ambient pressure port, wherein the inspiration valve and the expiration valve are fluidly connected to the ambient port.

5. The valve structure of claim 1, further comprising:

an inlet pressure valve that is constructed to allow the first air flow from the air flow generator into the mask with substantially no resistance and to block the second air flow from within the mask to the air flow generator.

6. The valve structure of claim 1, wherein the valve structure is a cartridge.

7. The valve structure of claim 1, wherein the valve structure is removable from the mask.

8.

A valve structure for treating a patient suffering from obstructive sleep apnea, the valve structure adapted to be connected to an air flow generator and connected to a mask that covers at least the nostrils of a patient, the valve structure comprising:

an inlet pressure port constructed to be attached to the air flow generator;

an inlet pressure valve connected to an inside of the mask and to the inlet pressure port;

an expiration valve connected to the inlet pressure port comprising an expiratory membrane constructed to prevent a second air flow across the membrane, and a primary seat and a secondary seat;

an inspiration valve fluidly connected to the inside of the mask and to an outside of the mask;

an opening fluidly connected to the secondary seat and the outside of the mask;

the valve structure having at least an inspiration mode, a rest/apnea mode and an expiration mode;

the inspiration mode occurs when the patient inspires air, during which the inspiration valve and the inlet pressure valve are open, and the expiratory membrane forms a seal with the primary seat directing a first air flow around the expiratory membrane;

the rest/apnea mode occurs when the patient is neither inspiring air nor expiring air, during which the inlet pressure valve is open, the expiratory membrane forms a seal with the primary seat directing the first air flow around the expiratory membrane, and inspiration valve are closed; and the expiration mode occurs when the patient expires air, during which the expiratory membrane forms a seal with the secondary seat directing the second air flow around the expiratory membrane, a portion of air flow from the air flow from the airflow generator passes over the secondary seat and through the opening, and the inlet pressure valve and the inspiration valve are closed.

9. The valve structure of claim 8, wherein the valve structure further comprises a disconnected mode when the air flow generator is not providing air flow to the valve structure:

during which when a patient inspires, the inspiration valve opens, and the expiratory membrane forms a seal with the primary seat; and during which when a patient expires, the inspiration valve is closed, and the expiratory membrane forms a seal with the secondary seat.

10. The valve structure of claim 8, wherein the valve structure further comprises a disconnected mode when the air flow generator is not providing air flow to the valve structure:

during which, when a patient inspires, the inspiration valve is open; and during which, when a patient expires, the inspiration valve is closed.

11.

A system for treating a patient suffering from obstructive sleep apnea, system comprising:

an air flow generator;

a tube connected to the air flow generator;

a mask constructed to cover at least the nostrils of the patient, the mask comprising:

an inlet pressure port constructed to be attached to the air flow generator;

an expiration valve comprising an expiratory membrane constructed to prevent a second air flow across the membrane and a primary seat and a secondary seat, wherein during inspiration by the patient the expiratory membrane forms a seal with the primary seat directing air a first flow around the expiratory membrane, and wherein during expiration by the patient the expiratory membrane forms a seal with the secondary seat directing the second air flow around the expiratory membrane;

an opening constructed to evacuate a portion of air flow from the air flow generator over the secondary seat to an outside of the mask, during expiration; and an inspiration valve constructed to allow air flow from the outside of the mask into the mask with substantially no resistance and block air flow from within the mask to the outside of the mask.

12.

The system of claim 11, wherein the expiratory valve further comprises an opening pressure, and the opening pressure is variable and dependent on a pressure of air in the inlet pressure port as follows: (1) the opening pressure of the expiration valve increases when the pressure of air in the inlet pressure port increases; and/or (2) the opening pressure of the expiration valve decreases when the pressure of air in the inlet pressure port decreases.

13. The system of claim 12, wherein the air flow generator further comprises a controller that adjusts an air flow pressure and volume to be generated.

14. The system of claim 13, wherein the controller comprises a delay circuit that delays the generation of air flow from the air flow generator for a predetermined amount of time.

15. The system of claim 14, wherein a predetermined maximum pressure is set and the air flow generator gradually increases the pressure of air generated until the maximum pressure is reached.

16. The system of claim 14, further comprising a sleep detector that signals the controller that the patient is asleep, thus activating the generation of air flow from the air flow generator.

17. The system of claim 16, wherein a predetermined maximum pressure is set, and the air flow generator gradually increases the pressure of air generated until the maximum pressure is reached.

18. The system of claim 16, wherein the sleep detector is worn by the patient and is adapted to take biometric readings of the patient.

19. The system of claim 16, wherein the sleep detector is wirelessly connected to the controller.

20. The system of claim 11, wherein the inspiration valve comprises two valves.

21. The system of claim 11, wherein the mask further comprises an ambient pressure port, wherein the inspiration valve and the expiration valve are fluidly connected to the ambient port.

22. The system of claim 11, wherein the mask further comprises an inlet pressure valve that is constructed to allow air flow from the air flow generator into the mask with substantially no resistance and block air flow from within the mask to the air flow generator.

23. The system of claim 22, wherein the expiration valve, the inspiration valve, and the inlet pressure valve are part of a cartridge that is removable from the mask.

24. The system of claim 11, wherein the expiration valve is part of a cartridge that is removable from the mask.

25. The system of claim 11, wherein the expiration valve and the inspiration valve are part of a cartridge that is removable form the mask.

* * * * *